United States Patent
Auld et al.

(10) Patent No.: US 10,426,111 B2
(45) Date of Patent: Oct. 1, 2019

(54) LOW PALMITIC ACID COTTON LINES

(71) Applicant: Texas Tech University System, Lubbock, TX (US)

(72) Inventors: Dick L. Auld, Lubbock, TX (US); Bralie Renae Hendon, Welch, TX (US)

(73) Assignee: TEXAS TECH UNIVERSITY SYSTEM, Lubbock, TX (US)

( * ) Notice: Subject to any disclaimer, the term of this patent is extended or adjusted under 35 U.S.C. 154(b) by 348 days.

(21) Appl. No.: 14/917,796

(22) PCT Filed: Sep. 8, 2014

(86) PCT No.: PCT/US2014/054576
§ 371 (c)(1),
(2) Date: Mar. 9, 2016

(87) PCT Pub. No.: WO2015/035312
PCT Pub. Date: Mar. 12, 2015

(65) Prior Publication Data
US 2016/0222399 A1 Aug. 4, 2016

Related U.S. Application Data

(60) Provisional application No. 61/875,531, filed on Sep. 9, 2013.

(51) Int. Cl.
| | |
|---|---|
| *A01H 6/60* | (2018.01) |
| *A01H 5/10* | (2018.01) |
| *A01H 1/04* | (2006.01) |
| *A01H 5/02* | (2018.01) |
| *A01H 1/06* | (2006.01) |
| *A01H 1/02* | (2006.01) |

(52) U.S. Cl.
CPC ............... *A01H 5/02* (2013.01); *A01H 1/02* (2013.01); *A01H 1/04* (2013.01); *A01H 1/06* (2013.01); *A01H 5/10* (2013.01); *A01H 6/604* (2018.05)

(58) Field of Classification Search
None
See application file for complete search history.

(56) References Cited

U.S. PATENT DOCUMENTS

| | | | |
|---|---|---|---|
| 7,619,105 B2 * | 11/2009 | Green | A01H 5/10 435/190 |
| 2008/0092255 A1 | 4/2008 | Edgerton et al. | |
| 2009/0055962 A1 | 2/2009 | Auld et al. | |
| 2010/0218278 A1 | 8/2010 | Kaster, Jr. et al. | |
| 2011/0223311 A1 | 9/2011 | Liu et al. | |

OTHER PUBLICATIONS

Bechere et al 2009 (Crop Sci 49: p. 1586-1592). Of record from International search report.*
Bechere, Efrem, et al.; Development of "naked-tufted" seed coat mutants for potential use in cotton production; Euphytica (2009) 167:333-339; Published Jan. 30, 2009; 7 pages.
Bechere, Efrem, et al.; Imazamox Tolerance in Mutation-Derived Lines of Upland Cotton; Crop Science, vol. 49, Sep.-Oct. 2009, www.crops.org, pp. 1586-1592, 7 pages.
Authorized Officer Blaine R. Copenheaver; International Search Report and Written Opinion, dated Dec. 31, 2014; 18 pages.

* cited by examiner

*Primary Examiner* — Matthew R Keogh
(74) *Attorney, Agent, or Firm* — Dickinson Wright PLLC; Kristopher Lance Anderson

(57) ABSTRACT

Disclosed is an invention of cotton lines 2-340/1-1422, 1-1422/SCM 3-7-3, 1-1422/2-340, 1-136/2-340, AFIS 1-1422. AFIS 2-340, AFIS 1-136, and SCM 3-7-3, and relates to seeds, plants, plant cells, plant tissue and harvested products, lint, and oil, as well as to hybrid cotton plants and seeds and other plants, cultivars, and varieties produced by essentially deriving such plants, cultivars, and varieties from cotton lines 2-340/1-1422, 1-1422/SCM 3-7-3, 1-1422/2-340, 1-136/2-340, AFIS 1-1422, AFIS 2-340, AFIS 1-136, and SCM 3-7-3. The present invention particularly relates to the development of specific cotton lines for the regulation of palmitic acid for the production of seeds having cottonseed oil content with reduced levels of palmitic acid. The cotton lines of the present disclosure have lower levels of palmitic acid content, and allows for the germination of seed at lower soil temperatures than current commercially available cotton cultivars.

19 Claims, 12 Drawing Sheets

FIG. 2

| Species/Type | Genetics (Reference) | C16:0 | C18:0 | C18:1 | C18:2 | C18:3 |
|---|---|---|---|---|---|---|
| | | ---% Methyl Esters--- | | | | |
| Cotton | Conventional (Liu) | 26 | 2 | 13 | 58 | --- |
| High C18:0 | Transgenic (Liu) | 17 | 38 | 10 | 38 | --- |
| Mid C18:1 | Transgenic (Liu) | 25 | 2 | 40 | 33 | --- |
| High C18:1 | Transgenic (Liu) | 17 | 1 | 78 | 4 | --- |
| | | | | | | |
| Soybeans | Conventional (Primomo) | 11 | 4 | 20 | 57 | 9 |
| Low C16:0 | Mutant (2) (Primomo & Fehr) | 5 | 4 | 21 | 61 | 10 |
| | Mutant (1) (Primomo & Fehr) | 7 | 4 | 22 | 58 | 10 |
| High C16:0 | Mutant (Primomo) | 16 | 4 | 18 | 51 | 11 |
| | Mutant (Primomo) | 16 | 4 | 18 | 53 | 10 |
| Mid C18:1 | Mutant (Primomo) | 10 | 4 | 34 | 42 | 9 |
| High C18:1 | Transgenic (Fehr) | 6 | 4 | 85 | 1 | 2 |
| Low C16:0/C18:3 | Mutant (Primomo) | 4 | 3 | 21 | 67 | 5 |

FIG. 4

| Line | Pedigree | C16:0/C16:0 | Purpose |
|---|---|---|---|
| 2004 - CB 1 | TTU 201-3S/TTU 161-6S | (19.2/18.5) | Low C16:0 X Low C16:0 |
| 2004 - CB 2 | TTU 203-5S/TTU 157-7S | (17.1/18.6) | Low C16:0 X Low C16:0 |
| 2004 - CB 6 | TTU 207-5S/TTU 161-6S | (18.7/18.5) | Low C16:0 X Low C16:0 |
| 2004 - CB 7 | TTU 285-11S/TTU 157-7S | (17.1/18.6) | Low C16:0 X Low C16:0 |
| 2004 - CB 8 | TTU 201-3S/TTU 157-7S | (19.2/18.1) | Low C16:0 X Low C16:0 |
| 2004 - CB 9 | TTU 285-11S/TTU 201-3S | (17.1/19.2) | Low C16:0 X Low C16:0 |
| 2004 - CB 3 | FM 958/TTU 157-9S | --- | High Yield X Low C16:0 |
| 2004 - CB 4 | FM 958/Sphinx 86-4-2S | --- | High Yield X Low C16:0 |
| 2004 - CB 5 | FM 958/Atlas 263-1-2S | --- | High Yield X Low C16:0 |
| 2004 - CB 10 | FM 958/TTU 161-6S | --- | High Yield X Low C16:0 |
| 2004 - CB 12 | FM 958/SC 9023 P 179-4-1S | --- | High Yield X Low C16:0 |
| 2004 - CB 15 | FM 958/TTU201 3S | --- | High Yield X Low C16:0 |
| 2004 - CB 14 | FM 958/Explorer 162-5-2S-9 | --- | High Yield X Low C16:0 |
| 2004 - CB 16 | FM 958/Atlas 251-1-3S-2 | --- | High Yield X Low C16:0 |

FIG. 5

|  | 1995/98 FA Composition[‡] | | | | Estimated Melting Pt | Seedlings at 59°F | |
|---|---|---|---|---|---|---|---|
|  | 16:0 | 18:0 | 18:1 | 18:2 | | Germination | Radical Length |
| Low Melting Point: | — % Methyl Esters — | | | | —°F— | — % — | — in — |
| TTU 285 | 19.0 | 2.2 | 18.6 | 56.5 | 55.6 | 76 a-d[†] | 9.6 abc[†] |
| TTU 157 | 20.7 | 2.5 | 18.7 | 54.3 | 58.3 | 76 a-d | 12.2 a |
| TTU 161 | 20.3 | 2.4 | 20.1 | 53.5 | 58.1 | 68 a-d | 10.8 ab |
| TTU 201 | 20.2 | 2.7 | 19.5 | 53.3 | 58.1 | 72 a-d | 7.4 b-e |
| TTU 207 | 20.8 | 2.3 | 19.6 | 53.6 | 58.3 | 88 a | 11.9 a |
| Average | 20.2 | 2.4 | 19.3 | 54.2 | 57.7 | 76 | 10.4 |
| High Melting Point: | | | | | | | |
| TTU 39 | 24.9 | 2.6 | 18.6 | 49.2 | 63.5 | 52 d | 5.3 d-e |
| TTU 254 | 25.2 | 2.6 | 18.5 | 50.3 | 63.9 | 56 cd | 6.6 cde |
| TTU 81 | 25.6 | 2.7 | 18.7 | 48.8 | 64.4 | 60 bcd | 8.2 a-e |
| TTU 28 | 25.0 | 2.7 | 20.0 | 48.2 | 64.0 | 24 e | 7.6 b-e |
| Average | 25.2 | 2.7 | 19.0 | 49.1 | 64.0 | 48 | 6.9 |
| Varieties: | | | | | | | |
| Aggie Cotton | 24.3 | 2.4 | 17.5 | 51.9 | 62.1 | 80 abc | 10.1 abc |
| PM 280 | 24.0 | 2.6 | 18.7 | 51.4 | 62.2 | 84 ab | 9.1 a-d |
| HS 200 | 24.9 | 2.8 | 19.3 | 50.7 | 63.7 | 20 e | 4.4 e |
| Average | 24.4 | 2.6 | 18.5 | 51.3 | 62.6 | 61 | 7.9 |

[†]Means within a column not followed by the same letter differ at the 0.05 level of probability by Fisher's Protected Least Significant Difference Test.

[‡]16:0 - Palmitic Acid (MP = 145°F); 18:0 - Stearic Acid (MP = 157°F); 18:1 - Oleic Acid (MP = 36°F); and 18:2 - Linoleic Acid (MP = 23°F)

FIG. 10

Fatty Acid Composition of Cottonseed

|  | C16:0 | C18:0 | C18:1 | C18:2 |
|---|---|---|---|---|
|  | ---------------- % Methyl Ester ---------------- | | | |
| Commercial: | | | | |
| DP 0912 B2RF | 25.7 | 2.3 | 24.5 | 47.5 |
| FM 9058 F | 23.6 | 2.9 | 30.5 | 43.0 |
| PHY 499 WRF | 20.9 | 2.2 | 32.5 | 44.4 |
| Parental Lines: | | | | |
| AFIS1-136-A16 | 17.9 | 2.2 | 15.7 | 62.1 |
| AFIS1-1422-A5 | 18.1 | 2.7 | 18.0 | 58.7 |
| AFIS2-340-A5 | 18.2 | 2.2 | 18.7 | 58.1 |
| SCM3-7-3-A3 | 18.7 | 1.9 | 20.0 | 56.8 |
| Selected Lines: | | | | |
| 1-1422/2-340 (3-3) | 17.3 | 2.7 | 27.7 | 51.7 |
| 1-1422/SCM (1-1) | 17.2 | 2.7 | 23.5 | 56.7 |
| 2-340/1-1422 (3-16) | 17.8 | 2.6 | 24.7 | 54.9 |

FIG. 12

FBRI No: 114394

HVI Test Data
Project: 9262

| Population | Line | Rep | Sample | MIC | LENGTH | UNIF. | STRENGTH | ELON. | Rd | +b | CGRD | LEAF |
|---|---|---|---|---|---|---|---|---|---|---|---|---|
| AFIS LP | AFIS A 136 | 1.0 | 22 | 4.2 | 1.29 | 85.5 | 35.6 | 7.7 | 81.7 | 7.5 | 21-2 | 3 |
| AFIS LP | AFIS A 136 | 1.0 | 23 | 4.0 | 1.28 | 86.7 | 36.8 | 8.1 | 79.8 | 8.7 | 21-1 | 3 |
| AFIS LP | AFIS A 1422 | 1.0 | 24 | 5.0 | 1.14 | 83.0 | 32.7 | 7.6 | 80.7 | 7.8 | 21-2 | 2 |
| AFIS LP | AFIS B 340 | 1.0 | 21 | 4.2 | 1.20 | 83.8 | 37.3 | 7.4 | 79.6 | 6.4 | 31-2 | 6 |
| AFIS LP | EM 4-3-1 | 1.0 | 3 | 4.8 | 1.02 | 79.5 | 28.4 | 7.7 | 81.8 | 7.6 | 21-1 | 2 |
| AFIS LP | RM 3-8-1 | 1.0 | 2 | 4.5 | 1.05 | 83.5 | 29.6 | 10.1 | 76.6 | 8.0 | 31-2 | 6 |
| AFIS LP | SCM 3-4-3 | 1.0 | 4 | 5.4 | 1.05 | 82.7 | 30.5 | 8.5 | 81.7 | 7.9 | 21-1 | 4 |
| AFIS LP | SCM 3-7-3 | 1.0 | 1 | 4.6 | 1.08 | 84.6 | 30.5 | 9.2 | 81.6 | 7.1 | 31-1 | 4 |

LOW PALMITIC ACID COTTON LINES

CROSS-REFERENCE TO RELATED PATENT APPLICATIONS

This Application is the 35 U.S.C. § 371 National Application of International Patent Application No. PCT/US2014/054576, entitled "Low Palmitic Acid Cotton Lines." filed Mar. 8, 2014, which designated the United States and claimed priority to: provisional U.S. Patent Application Ser. No. 61/875,531, filed on Sep. 9, 2013, entitled "Low Palmitic Acid Cotton Lines," which provisional patent application is commonly assigned to the Assignee of the present invention and is hereby incorporated herein by reference in its entirety for all purposes.

This application includes material that is subject to copyright protection. The copyright owner has no objection to the facsimile reproduction by anyone of the patent disclosure, as it appears in the Patent and Trademark Office files or records, but otherwise reserves all copyright rights whatsoever.

This application includes material that is subject to copyright protection. The copyright owner has no objection to the facsimile reproduction by anyone of the patent disclosure, as it appears in the Patent and Trademark Office files or records, but otherwise reserves all copyright rights whatsoever.

TECHNICAL FIELD

The present disclosure relates in general to the field of cotton breeding and development. In particular, the present disclosure relates to cotton lines having low palmitic acid content, their progeny, and methods of making the same.

STATEMENT OF FEDERALLY FUNDED RESEARCH

None.

BACKGROUND

Because of the large global volume of cotton crops grown primarily for fiber production, cottonseed is available in substantial quantities in many parts of the world (Green, et al., 2002). In addition to the fiber production, from the crushing of this seed, around four million tons of cottonseed oil are produced annually, making it the sixth most important plant oil in commerce.

Cottonseed oil is the second most valuable product of cotton behind lint. World cottonseed oil production ranks third behind soybean and canola oil (USDA-FAS, 2013) It's has a distinct 2:1 polyunsaturated to saturated fatty acid composition that makes it an excellent salad and cooking oil with a neutral slightly nutty taste that generally consists of 26% saturated palmitic acid (C16:0), 2% saturated stearic (C18:0), 18% monounsaturated oleic acid (C18:1), and 52% polyunsaturated linoleic acid (C18:2) (www.cottonseed.com).

Cottonseed oil is a valued raw material in the food industry because its high level of the saturated palmitic acid and absence of the unstable linolenic acid (C18:3) impart good stability and flavor properties. However cottonseed oil is often partially hydrogenated to lower the level of polyunsaturates and achieve the very high stability required in deep-frying or the solidity required for margarine hard stock. Thus, partially hydrogenated cottonseed oil contains a relatively high level of nutritionally undesirable saturated and trans fatty acids. Genetic improvement of cottonseed oil fatty acid composition is therefore being sought to avoid the need for hydrogenation and thereby to improve the nutritional value of cottonseed oil products.

Previous studies have focused on manipulating various oil contents for desirable qualities. Transgenic cotton plants have been developed to increase levels of oleic acid (Chapman, et al., 2001). Commercialization of high-laurate canola and high-oleic soybeans has further confirmed the potential of such manipulation in the food and agricultural markets. Liu, et al., 2009, further suggests that the ability to control levels of oleic and stearic acids through RNAi silencing of certain genes opens up the possibility of designer fatty acid compositions through combined and controlled silencing of genes.

Sawan et al. (2001) tested the effects of nitrogen fertilization, plant growth regulators, and zinc on oil properties of cottonseed. All three treatments resulted in a significant decrease in the saturated fatty acids and simultaneously increasing the unsaturated fatty acids.

Green (1986) was able to lower linolenic fatty acid (18:3), using two mutant genotypes of flax (Linum usitatissimum L.) that were treated with EMS. The parental lines contained 19.1 and 23.4% linolenic acid. By crossing the parents he was successfully able to decrease the total C18:3 to 7%. 7% of the $F_2$ progeny had low C18:3 ($\frac{1}{16}^{th}$) which proved the recombination of two unlinked genes. There were four phenotypic classes suggesting additive gene action. When tested in $F_3$ generation the low linolenic lines did not segregate, proving they were homozygous recessive for both mutations.

Li et al. (2002) stated that several mutant lines of soybeans contain reduced levels of palmitic acid had genes for palmitic acid located at different loci in the soybean genome, They were able to locate two genes in soybeans using molecular mapping, that when combined accounted for 51% of the total phenotypic variation for palmitic acid in the $F_2$ population and 43% of the variation in the $F_{2,3}$ generation.

Miquel et al. (1993) researched the fad2 gene in Arabidopsis and its effects on germination, as well as growth and development. The fad2 gene reduces the amount of polyunsaturated fatty acids in the seed oil, by altering the pathway and creating a higher concentration of the monounsaturated fatty acid, oleic acid. The polyunsaturated fatty acids linolenic and linoleic have a much lower melting temperature than oleic. Miquel and Browse (1994) tested mutant lines of Arabidopsis that contained the fad2-2 gene. Lines were subjected to temperatures of 22° C. (72° F.) then moved to low temperatures of 6° C. (43° F.). Wild-type, and heterozygous lines had excellent germination compared to the homozygous lines that contained the fad2 gene, meaning that the wild-type, containing higher levels of polyunsaturated fatty acids, had a higher tolerance to cool temperatures.

Many studies have further shown the correlation of seed oil content and certain traits, including chilling sensitivity, as cold tolerances if of significant economic value (Nishida, 1996). It is well established that seed oil content affects the membrane lipids, and the level of saturation of such membrane lipids has been correlated to such chilling tolerance.

Additional studies have attempted to show a correlation of percentage fat content within a seed and its cold tolerance, with the intent of obtaining the knowledge of the distribution of the fatty acids in phospholipids of germinating seeds of chilling-sensitive and chilling-resistant plant species may contribute to an understanding of plant susceptibility to chilling injury (Hall, 2003). Adaptation of cotton to low temperatures has been correlated to microsomal omega-6 desaturase (FAD2), as a responsible enzyme for membrane lipid modification (Kargiotidou, 2008). It has further been proposed that plants with lower seed oil melting points and proportions of saturated fatty acids should germinate at cooler temperatures (Meadows, 2012). Linder (2000) even suggests that the proportion of saturated fatty acids in triacylglycerols be suitable as a proxy for melting point, and that such proportions of saturated fatty acids are reduced at higher latitudes. It has therefore been a continued focus to change the proportion of saturated fatty acids to impact the melting point of the overall oil composition.

Because germination temperature is of significant economic interest, the correlations of saturated fatty acid content to melting point have been pursued. However, while indirectly achieved by the increase of oleic acids (see Liu, et al., 2002) which was suggestive of cold tolerance, results have been inconclusive. Meadows (2012) showed inconclusive results in confirming the expectation of germination temperature and the melting point of seed oils. To date, efforts have primarily focused on enhancing the levels of non-saturated oils to further decrease the saturated oils; or, alternatively, to diminish generally the proportions of saturated oil content in the seed. There remains a need in the art for determining optimized levels of oils, including determining which oils are responsible for increased germination at lower temperatures, without affecting the integrity or stability of the seed or resulting plants.

In addition to the economic benefits of the cottonseed oil, cotton producers in northern regions are often faced with very short growing seasons, requiring optimum conditions for increased quality and yields of the cotton, crop. Cotton production in many northern regions is limited by 1) poor stand establishment caused by cool spring temperatures; 2) the lack of heat units in the short growing season; 3) and very cool fall temperatures. Bolek (2010) stated that the ability of cotton to establish a stand of vigorous seedlings under cool temperatures is a key component in the production of cotton in areas experiencing cool temperatures during the early seedling stages. Also due to cotton's indeterminate growth habit an early frost in the fall can be detrimental to cotton fiber and seed quality. Consequently, the ability for a producer to have increased flexibility with planting date would be very beneficial.

While some commercial varieties are more capable of germinating at lower temperatures, there are currently no solutions on the market which provide for cotton lines capable of producing cotton cultivars having seed with low saturated fatty acid content for cottonseed oil production or enhanced germination percentages at significantly lower soil temperatures.

SUMMARY OF THE DISCLOSURE

The present disclosure addresses failings in the art by providing low palmitic acid cotton lines with significantly reduced levels of palmitic acid. The present disclosure enables the regulation of palmitic acid levels in cottonseed triaclglycerols (TAGs) due to mutations in enzymes of the biosynthetic pathway. Like all, plants, fatty acids are synthesized in developing cottonseeds in the plastid compartment in two-carbon increments by a multi-enzyme fatty acid synthase complex. Chain length terminating enzymes, the ACP thioesterases, release fatty acids from the plastid for export to the ER for tryglycerol assembly. The composition of fatty acids released from the plastids is then determined by the relative activity of these enzymes. The resultant low palmitic acid lines further exhibit germination at lower soil temperatures.

The present disclosure relates to seeds, plants, plant cells, parts of plants, cotton lint or fiber, and cotton textiles of cotton lines: 2-340/1-1422; 1-1422/SCM 3-7-3; 1-1422/2-340; 1-136/2-340; AFIS 1-1422; AFIS 2-340; AFIS 1-136-A5, a seed sample of said cotton line having been deposited in ATCC Accession No. PTA-126033 ; and SCM 3-7-3, including seed samples of said cotton lines, well as to hybrid cotton plants and seeds obtained by crossing plants of said cotton lines with other cotton plants.

The present disclosure further encompasses plants and plant lines produced by the method of derivation or essential derivation from plants of 2-340/1-1422; 1-1422/SCM 3-7-3; 1-1422/2-340; 1-136/2-340; AFIS 1-1422; AFIS 2-340; AFIS 1-136-A5, a seed sample of said cotton line having been deposited in ATCC Accession No. PTA-126033; and SCM 3-7-3, and to plants of said lines reproduced by vegetative methods, including but not limited to regeneration of embryogenic cells or tissue.

The present disclosure also encompasses methods of producing cotton seeds that comprise crossing plants of cotton lines 2-340/1-1422; 1-1422/SCM 3-7-3; 1-1422/2-340; 1-136/2-340; AFIS 1-1422; AFIS 2-340; AFIS 1-136-A5, a seed sample of said cotton line having been deposited in ATCC Accession No. PTA-126033; or SCM 3-7-3, either with itself or with a second, distinct cotton plant or line.

The present disclosure further utilizes mutagenesis to develop cotton lines with low palmitic acid content. Chemical mutagenesis has been shown to be an ideal tool for manipulating fatty acid composition in higher plants (Auld, et al., 1992) Embodiments of the present disclosure shows that cottonseed lines with even a modest 5% reduction of palmitic acid (25% to 20%) show faster emergence and longer radical lengths when grown at 59° F. (FIG. 5). The oil in these "low palm" lines have a reduced estimated melting temperature of the seed storage oil of 57.77° F. compared to over 62° F. for normal cottonseed oil. From studies, a single "low palm" mutant allele in cotton will reduce the palmitic acid content by approximately 4 to 5%. Combining two separate "low palm" alleles would potentially reduce the cottonseed storage oil estimated melting point to 47° F. The impact of "double low palm" alleles suggests that fatty acid biosynthesis in cotton is controlled by a genetic system similar to other tropical origin crops such as soybeans (Fehr, 2007). The present disclosure suggests eight lines initially identified are complimentary and result in a further reduction of palmitic acid in cotton seed.

The present disclosure provides for cotton lines capable of producing seed having low-palmitic acid content in relation to the total oil content of the seed. The cotton lines may be in the form of a plant, or a part thereof, or may be in the form of a tissue culture produced from a plant part selected from the group consisting of leaf, pollen, ovule, embryo, cotyledon, hypocotyl, meristematic cell, root, root tip, pistil, anther, flower, seed, shoot, stem, pod and petiole.

The present disclosure may further provide methods for producing the cotton plant by crossing two cotton plants and harvesting the resultant cotton seed, wherein at least one plant is a cotton plant having low-palmitic acid content, such as the identified lines identified herein.

The present disclosure enables the production of a mutant line that produces a seed comprising a palmitic acid content of less than 22% of the total oil content of the seed. The present disclosure further enables the production of a mutant line that produces a seed comprising a palmitic acid content of less than 20% of the total oil content of the seed. The present disclosure further enables the production of a mutant line that produces a seed comprising a palmitic acid content of less than 17% of the total oil content of the seed. The present disclosure further enables the production of a mutant line that produces a seed comprising a palmitic acid content of about 15% of the total oil content of the seed.

The present disclosure further provides a method of producing a cotton plant having seeds containing low-palmitic acid, wherein said method comprises; (a) inducing mutagenesis in at least some cells from a plant, more particularly of a cotton plant, that has a palmitic acid content of less than 22%; (b) regenerating plants from at least one of said mutagenized cells; (c) selecting regenerated plants which capable of producing seed having a low palmitic acid, and (d) deriving further generations of plants from said regenerated plants.

The present disclosure further provides a method of producing a cotton plant with modified fatty acid metabolism, wherein the method comprises mutagenesis, such as which suppresses one or more fatb genes encoding acyl-ACP thioesterase in the cotton lines of the present disclosure.

The present disclosure provides methods for introducing a desired trait into a cotton cultivar, wherein the method comprises: (a) crossing a low-palmitic cotton mutant line, with a plant of another cotton cultivar that comprises a desired trait, wherein said desired trait is selected from the group consisting of modified palmitic acid percent; (b) selecting one or more progeny plants that have the desired trait; (c) backcrossing the selected progeny plants with the selected low-palmitic acid mutant line in (a) above; (d) selecting for backcross progeny plants that have the desired trait; and (e) repeating steps (c) and (d) two or more times in succession to produce selected third or higher backcross progeny plants that comprise the desired trait and otherwise comprise essentially all of the physiological and morphological characteristics of the low-palmitic acid cotton mutant line selected in (a) above.

The methods set forth above utilizes know mutagens such as ethyl methanesulfonate (EMS), gamma-rays, and sodium azide. In particular, the present disclosure provides for a method wherein the mutagenesis is induced by means of EMS treatment.

Further aspects of the present disclosure include methods for introducing a desired trait into a cotton cultivar utilizing transformation genetic transformation of regenerable plant tissue or embryogenic cell cultures of the said initial variety by methods well known to those skilled in the art, such as *Agrobacterium*-mediated transformation and other plant transformation methods.

Indeed, the present disclosure provides for the development of further generations of plants which include establishment of a commercial cotton cultivar, as discussed in more detail below.

BRIEF DESCRIPTION OF THE DRAWINGS

The foregoing and other objects, features, and advantages of the disclosure will be apparent from the following description of embodiments as illustrated in the accompanying figures and drawings. Additional tables are present throughout the disclosure.

FIG. 2 depicts modifications reported in fatty acid composition of storage oils of cotton and soybeans using either transgenic or mutational approaches.

FIG. 4 depicts fourteen lines developed for screening for allelic recombination for reduced levels of palmitic acid (C16:0) and/or increased lint and oil yields in upland cotton.

FIG. 5 depicts fatty acid composition, estimated melting point and germination and radical length at 59° F. of five low melting point mutants, four high melting point mutants and three commercial varieties of cotton.

FIG. 10 depicts fatty acid compositions of various lines and cultivars of cotton seed.

FIG. 12 depicts High Volume Instrument (HVI) data relating to the M5 lines of the present disclosure, particularly AFIS 1-1422, AFIS 2-340, AFIS 1-136-A5, and SCM 3-7-3. HVI systems based on the fiber bundle strength testing in which large numbers of fibers are tested with their average values determined.

DETAILED DESCRIPTION OF THE DISCLOSURE

Figure 1:
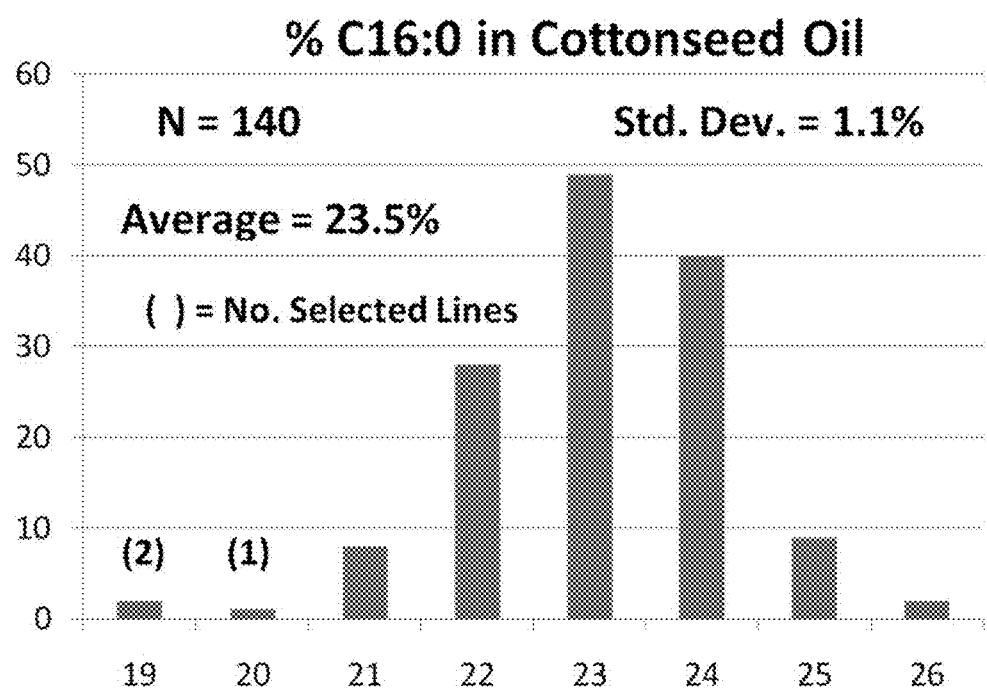
FIG. 1 depicts the distribution of percent palmitic acid in 140 mutant lines of cotton seed analyzed by the USDA-ARS Laboratory at New Orleans, La.
Figure 3:
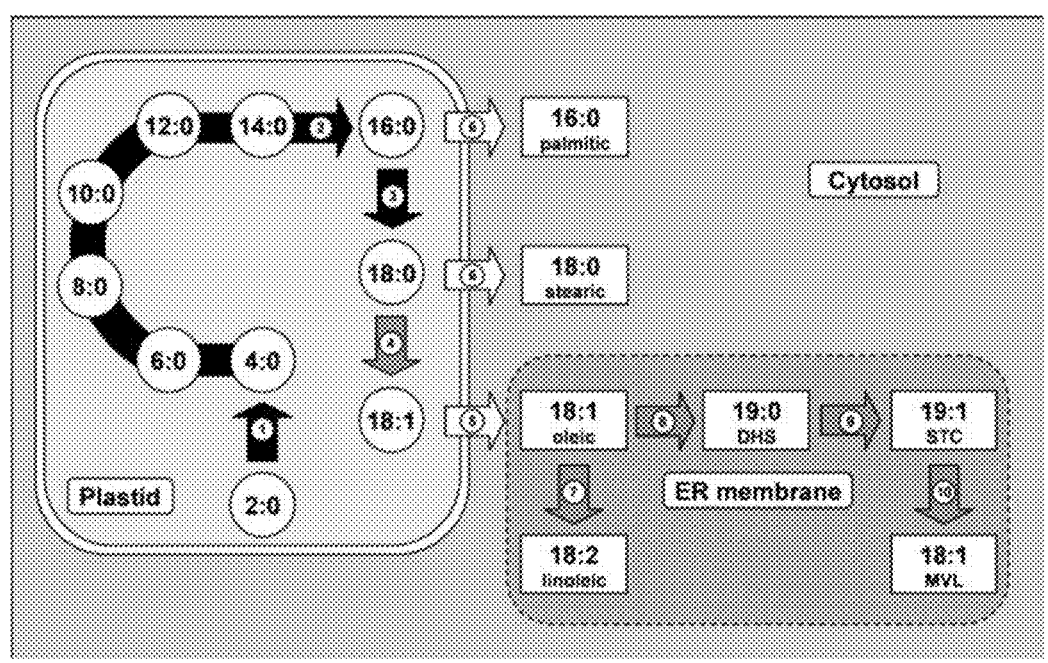
FIG. 3 A simplified schematic of fatty acid biosynthesis in developing cottonseed showing important enzymatic steps: 1. keto-acyl synthase III (KASIII), 2. keto-acyl synthase I (KASI), 3. keto-acyl synthase II (KASII), 4. 9-stearoyl-ACP desaturase (SAD), 5. oleoyl-ACP thioesterase, 6. acyl-ACP thioesterase, 7. 12-oleoyl-lipid desaturase (FAD2), 8. Cyclopropane fatty acid synthase (CPA-FAS), 9. cyclopropane fatty acid desaturase (CPA-DES), 10. alpha-oxidase. DHS: dihydrosterculic acid; STC, sterculic acid; MVL, malvalic acid. (Taken from Liu et al., 2009, in A. H. Paterson (ed.), Genetics and Genomics of Cotton, Plant Genetics and Genomics: Crops and Models 3, DOI 10.1007/978-0-387-70810-2_15, Springer Media.

While the making and using of various embodiments of the present disclosure are discussed in detail below, it should be appreciated that the present disclosure provides many applicable inventive concepts that can be embodied in a wide variety of specific contexts, goods, or services. The specific embodiments discussed herein are merely illustrative of specific ways to make and use the disclosure and do not delimit the scope of the disclosure.

All publications and patent applications mentioned in the specification are indicative of the level of skill of those skilled in the art to which this disclosure pertains. All publications and patent applications are herein incorporated by reference to the same extent as if each individual publication or patent application was specifically and individually indicated to be incorporated by reference.

The present disclosure will now be described more fully hereinafter with reference to the accompanying figures and drawings, which form a part hereof, and which show, by way of illustration, specific example embodiments. Subject matter may, however, be embodied in a variety of different forms and, therefore, covered or claimed subject matter is intended to be construed as not being limited to any example embodiments set forth herein; example embodiments are provided merely to be illustrative. Likewise, a reasonably broad scope for claimed or covered subject matter is intended. Among other things, for example, subject matter may be embodied as methods, compositions, processes, or systems. Accordingly, embodiments may, for example, take the form of seed, alleles, plants, mutant lines, or cultivars, or any combination thereof (other than naturally occurring compositions per se). The following detailed description is, therefore, not intended to be taken in a limiting sense.

Throughout the specification and claims, terms may have nuanced meanings suggested or implied in context beyond an explicitly stated meaning. Likewise, the phrase "in one embodiment" as used herein does not necessarily refer to the same embodiment and the phrase "in another embodiment" as used herein does not necessarily refer to a different embodiment. It is intended, for example, that claimed subject matter include combinations of example embodiments in whole or in part.

In general, terminology may be understood at least in part from usage in context. For example, terms, such as "and", "or", or "and/or," as used herein may include a variety of meanings that may depend at least in part upon the context in which such terms are used. Typically, "or" if used to associate a list, such as A, B or C, is intended to mean A, B, and C, here used in the inclusive sense, as well as A, B or C, here used in the exclusive sense. In addition, the term "one or more" as used herein, depending at least in part upon context, may be used to describe any feature, structure, or characteristic in a singular sense or may be used to describe combinations of features, structures or characteristics in a plural sense. Similarly, terms, such as "a," "an," or "the," again, may be understood to convey a singular usage or to convey a plural usage, depending at least in part upon context. In addition, the term "based on" may be understood as not necessarily intended to convey an exclusive set of factors and may, instead, allow for existence of additional factors not necessarily expressly described, again, depending at least in part on context.

Cotton is primarily grown for its fiber. Cottonseed accounts for approximately 20% of the total gross revenue. Misra and Bondurant (1999) stated that the sale of cottonseed typically offsets all or a segment of ginning cost. The two major consumers of cottonseed are oil mills and livestock producers, typically dairy farms. Cottonseed is priced on a grading system by the oil mills, which are graded on a base of 100-grade, anything less than this receives a discount.

For the purposes of the present disclosure cottonseed oil is the oil extracted from the seeds of cotton plants of various species, mainly *Gossypium hirsutum* and *Gossypium herbaceum*, that are grown for cotton fiber, animal feed, and oil. Cottonseed has a similar structure to other oilseeds such as sunflower seed, having an oil-bearing kernel surrounded by a hard outer hull; in processing, the oil is extracted from the kernel. Cottonseed oil is used for salad oil, mayonnaise, salad dressing, and similar products because of its flavor stability. Historically cottonseed oil has become the pre-eminent oil in the United States. Crisco and Wesson oil, which contain cottonseed oil, became direct substitutes for lard and other more expensive oils in baking, frying, sautéing, and salad dressings. By World War II cottonseed oil shortages forced the utilization of another direct substitute, soybean oil. By 1944, soybean oil production outranked cottonseed oil production due to cottonseed shortages and soybean oil costs falling below that of cottonseed oil. By 1950, soybean oil replaced cottonseed oil in the use of shortenings like Crisco due to soybeans comparatively low price. Prices for cottonseed were also increased by the replacement of cotton acreage by corn and soybeans, a trend fueled in large part by the boom in demand for corn syrup and ethanol. Cottonseed oil and production continued to decline throughout the mid and late 20th century.

In the mid to late 2000s, the consumer trend of avoiding trans-fats, and mandatory labeling of trans-fats in some jurisdictions, sparked an increase in the consumption of cottonseed oil, with some health experts and public health agencies recommending it as a healthy oil. Crisco and other producers have been able to reformulate cottonseed oil so it contains little to no trans-fats. Still, some health experts claim that cottonseed oil's high ratio of polyunsaturated fats to monounsaturated fats, and processed nature, make it unhealthy.

Currently, cottonseed oil ranks 6th in importance behind soybean, oil-palm, rapeseed, sunflower, and groundnut in global production of oilseeds (Liu et al., 2009; Green et al., 2009). Cottonseed contains approximately 25% oil and produces an oil that can be used as a food ingredient or as cooking oil. Cottonseed oil contains approximately 25% palmitic acid (C16:0), 2% stearic (C18:0), 18% oleic (C18:1), and 55% linoleic (C18:2) fatty acids. This is approximately 27% saturated fatty acid (palmitic and stearic acid), and 73% unsaturated fatty acid (oleic and linoleic acid). Since oleic fatty acid only has one carbon double bond it is often referred to as a monounsaturated fatty acid and linoleic with two carbon double bonds is a polyunsaturated fatty acid. Because of its high level of saturated fats, the nutritional value of cottonseed oil has been questioned (Green et al., 2009). Green et al. also stated that high levels of saturated fatty acids in a diet, especially palmitic fatty acid, contribute to increased blood cholesterol and increased low density lipoprotein (LDL), contributing to cardiovascular disease. Stearic acid is considered to be more neutral, not contributing to LDL or high density lipoprotein (HDL). If cotton genotypes with low palmitic acid were identified cottonseed oil could be a much more desirable product for human consumption.

Cottonseed at current pricing is approximately $248 per metric ton (USDA-NASS, 2012). If cotton contains 25% oil, this calculates to $0.487 per kg of oil or approximately $0.258 per liter. If this can be marketed as a more nutritional product, then with an increase to $0.379 per liter could mean a total increase of $115.21 per metric ton of cottonseed. This would take the 20% contribution of cottonseed to more around 28% of total gross returns.

Cotton breeders have typically focused their efforts on the improvement of lint yield and fiber quality parameters, while cottonseed oil has often been neglected. Liu et al. (2009) state that the nutritional and industrial value of cottonseed oil is determined by its fatty acid composition. Dowd et al. (2010) tested 35 genotypes, in six locations, in a two year study to compare the fatty acid compositions across locations. There results indicated that the genotype variances of palmitic, oleic, and linoleic were 62.4, 50.3, and 44.0%, respectively; the environmental variances were 33.7, 39.7, and 50.5% respectively; and the genotypexenvironment interaction variance of 3.9, 9.9, and 5.4% respectively. This means the gene controlling the synthesis of palmitic acid has a relatively high broad sense heritability, $H^2$=62.4%.

The FatB1 acyl-ACP thioesterase activity in cotton is thus responsible for the high level of palmitic acid incorporated into cottonseed oil (Pirtle et al., 1999). Jones et al. (1995)

identified the existence of two different types of thioesterases, designated as FatA and FatB, with substrate preferences for unsaturated or saturated acyl-ACPs, respectively.

Figure 6:
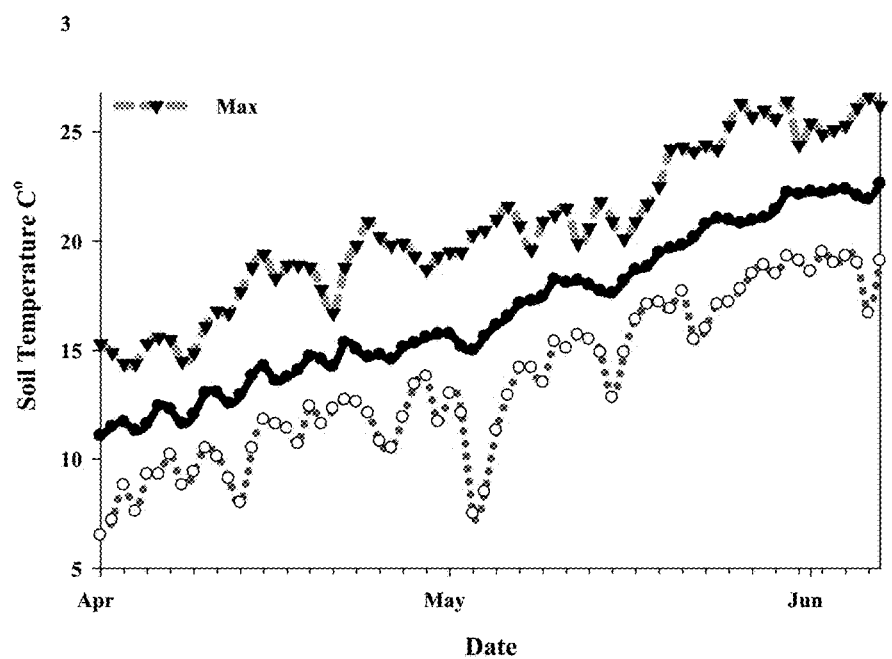
FIG. 6 depicts Average Soil Temperatures from 2000-2012 at 5.08 cm in Bushland, Tex. Source: USDA, NRCS (www.wcc.nrcs.usda.gov/)

Planting cotton earlier in the spring could allow higher yields, better fiber quality, and an earlier crop termination to avoid late season pests. According to Esparza et al. (2007) and Sansone et al. (2002), for every additional 41.7° C. (75° F.) heat units beyond 1000° C. (1800° F.) heat units cotton produces one more boll in non-water stressed plants. With germination results and fatty acid analysis performed, the prediction is the progeny of the low palmitic×low palmitic crosses which resulted in a homozygous recessive $F_2$ with a fatty acid composition of only 17% palmitic Acid to be able to germinate at temperatures as low as 12.8° C. (55° F.). This would mean that a producer in Bushland, Tex. could possibly plant as early as April $15^{th}$. Based on FIG. 6, a producer could plant on the April $15^{th}$ but is subject to risk of a decline in soil temperature. Thus, if a producer in this area is able to plant in the middle of April compared to middle of May, an additional 63° C. (113° F.) heat units is accumulated, and according to Esparza et al. (2007) and Sansone et al. (2002) in a non-water stressed cotton crop this would be an additional 1.50 bolls/plant. Oosterhuis et al. (1994) concluded that a cotton boll weights approximately 3-6 grams with 40% being lint weight. If a producer plants approximately 1.5 seeds/meter on 1 meter row spacings with a germination percentage of 80%, an additional 248 kg ha$^{-1}$ can be achieved. Heat Unit accumulation was documented from degreedays.net A monthly ten year average was derived to calculate monthly heat units, and a three year average for daily heat units was used to calculate a half month. Bushland, Tex. was used in this example for it was the only historical soil temperature data found from the Northern High Plains.

For the purposes of the present disclosure, germination percentage refers to how many seeds of a particular plant species, variety or seedlot are, or are likely to, germinate over a given set of conditions or criteria. It is a measure of germination time course and is usually expressed as a percentage, e.g., an 85% germination rate or percentage indicates that about 85 out of 100 seeds will probably germinate under the applicable conditions over the germination period given. On the other hand the number of seed able to complete germination in a population (i.e. seed lot) is referred as germination capacity.

Figure 7:
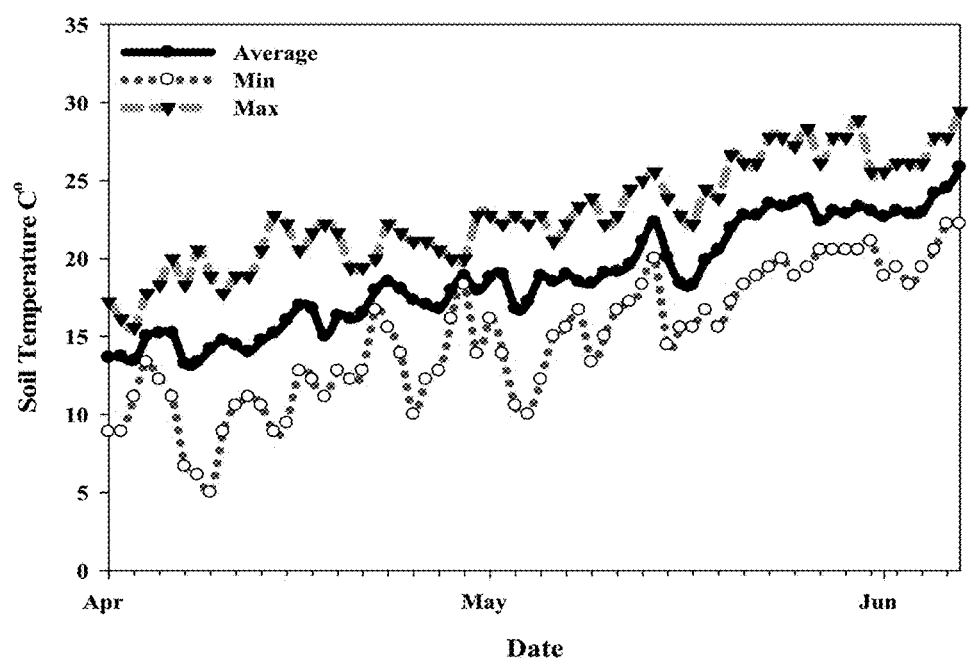
FIG. 7 depicts Average Soil Temperatures from 2005-2011 at 5.08 cm in Lubbock, Tex. Source: USDA, NRCS (www.wcc.nrcs.usda.gov/)
Figure 8:
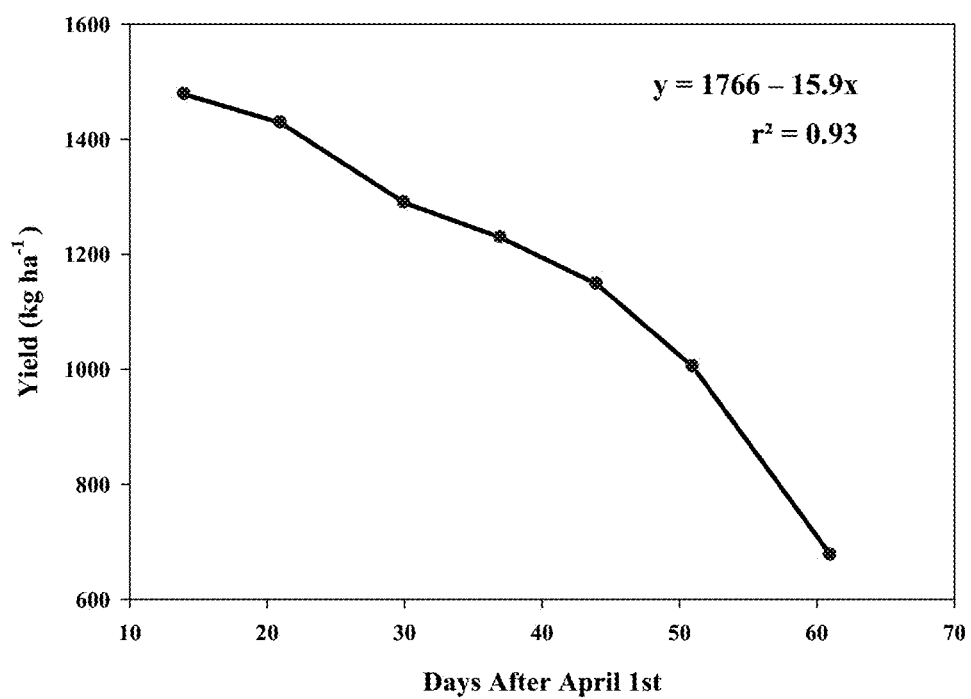
FIG. 8 illustrates a linear regression comparing yield and planting date.

FIG. 7 contains soil temperatures for the Lubbock Reese Center from 2005-2011. If a producer plants on April $15^{th}$ in Lubbock County, an additional 15-30 119.17° C. (215° F.) growing degree days can be achieved. By plugging in the additional heat units to the calculation above this means an approximate 471 additional kg ha$^{-1}$ compared to a May $15^{th}$ planting. By using the same configuration, yields based on additional heat unit accumulation was created for planting dates ranging from April $15^{th}$ though June $1^{st}$. With the results a regression model was created to show how planting date effects yield, (FIG. 8). This model shows that every day that cotton planting is delayed there is a total yield loss of 5.9 kg ha$^{-1}$. Other studies have confirmed that planting date has a great impact on cotton yield (Bilbro and Ray, 1973; Wrather et al., 2005; Hakoomat et al., 2009; Boquet and Clawson, 2009). From the yield data and planting dates from these studies a regression model was created to determine how delaying planting effects yield. From Bilbro and Ray (1973) resulted in an approximate loss of 12.03 kg ha$^{-1}$ per day, Wrather et al. (2005) results were very similar to Bilbro and Ray at 12.26 kg ha$^{-1}$. Hakoomat et al. (2009) experienced conditions that were a little different since the trial occurred in Pakistan, but still proved that delayed planting decreases yield with a loss of 7.57 kg ha$^{-1}$. Boquet and Clawson (2009) reported results in a more binomial regression compared to linear, which shows the optimal planting date falling middle to late April, but determined an estimated loss of 8.29 kg ha$^{-1}$.

It has been suggested that plants with a lower tolerance to cool temperatures contain higher proportions of di-saturated molecular species of PG than do those from chilling resistant species (Thomas, 1987). Lyons and Asmundson (1965) determined that there was a correlation between the percentage of unsaturated/saturated fatty acids of the mitochondrial membrane and chilling sensitivity. Baud (2010) reported that in angiosperms, triacylglycerols (TAGs) act as a reserve of carbon and energy allowing to fuel post-germinated seedling growth until photosynthesis occurs.

Breeding efforts are working vigorously to develop cultivars that have better yield components, fiber quality, as well as tolerance to abiotic and biotic stresses. With the low palmitic oil content, producers will be capable of planting in cooler soils ultimately increasing the growing season. Many studies have shown that planting date has a significant impact on cotton yield (Bilbro and Ray, 1969; Bilbro and Ray, 1973; Wrather et al., 2005; Hakoomat et al., 2009; Boquet and Clawson, 2009).

Marek and Bordovsky (2006) conducted a cotton research trial in Etter, Tex. to determine if cotton (*Gossypium hirsutum* L.) was a superior alternative to corn in the northern part of the Texas High Plains. With the depletion of the Ogallala Aquifer and new pumping regulations, alternative crops that are more water use efficient need to be analyzed. Marek and Bordovsky (2006) stated that by delaying planting until the latter part of May to early June, when soils are warmer, producers run the risk of having fewer growing degree-days and not fully maturing the crop. In their study it was concluded that due to the shorter growing season and early freeze, which averaged around October 15th, micronaire was severely affected. Cotton fiber that contains a micronaire value outside of the range 3.5 to 4.9 receives a discount penalty on their loan value. In their study, 3 of the 4 years received a discount. In the first year of the trial, early planting resulted in a substantial increase in average lint yield of 207 kg ha$^{-1}$. This difference was not seen in the other three years, possibly due to hormone herbicide drift that occurred in 2000 and 2002. The two planting dates attempted where approximately two weeks apart, except for 1999 which was almost a month, which could explain the substantial yield and fiber quality difference. Micronaire and fiber length uniformity were the only fiber quality parameters in the early planting that were statistically different from the later planting. The loan value was approximately 3.66 cents/kg higher for the early planting than the later planting. It was concluded in their study that no matter which cultivar was planted a lower micronaire value was expected. With the possibility of planting in April and an approximate 63 additional heat units ° C. can be acquired and a more desirable micronaire can be expected.

Wanjura et al. (2002) ran a regression on heat unit accumulation versus lint yields. Their study concluded that, with minimal water stress, lint yield was highly correlated with heat unit accumulation from May to September. 74% of the yield variation was due to heat units; with every additional heat unit an additional 0.96 kg ha$^{-1}$ was produced.

Peng et al. (1989) conducted a similar study which also resulted in cotton growth and development being directly associated with HU under irrigated conditions. Their study determined that with no water stress, heat units accounted for 90% of the variation in lint yield. When cotton plants became water stressed there was no significant correlation between yield and heat units. They also viewed yield components to see how lint yield was being increased. Their regression showed that 78% of yield variability was due to fruit number. The regression also showed that approximately 830 heat units ° C. were required to produce any yield and an increase of 1.12 kg ha$^{-1}$ per additional heat unit. A multiple-regression model was created with a dependent variable of lint yield and the independent variables heat units and water supply. The regression model was able to account for 93% of yield variation. Regression function was curvilinear in a manner similar to most production functions.

Sansone et al. (2002) describe heat units as the relationship between cotton development and the temperature. Equation 1 can be used to calculate heat units:

$$HU=((\text{MaxTemp}+\text{MinTemp})/2)-\text{basetemperature} \quad (\text{Eq. 1})$$

HU stands for heat unit, MaxTemp is the maximum air temperature for the day and MinTemp is the minimum air temperature for the day. The temperatures are divided by 2 to calculate a daily average temperature. Base temperature is recognized as the minimum temperature at which the plant will develop; in cotton the base temperature is 15.5° C. (60° F.). Temperatures below the base temperature will not reduce heat units nor will it reduce the plant's physiological maturity. Table A.1 demonstrates the number of required heat units for various developmental stages of cotton (Sansone et al., 2002). Cotton development stages are correlated to the air temperature throughout the growing season (Esparza et al., 2007).

Esparza et al. (2007) stated that some of the reasons for cotton production expanding into the northern Texas High Plains, Oklahoma, and Kansas are probably due to early maturing cultivars, rising energy costs, and declining water levels in the Ogallala Aquifer. Cotton production has expanded in this region where corn has predominately been produced (Colaizzi et al., 2004). Esparza et al. (2007) identified which counties in the northern High Plains of Texas, Oklahoma, and Kansas were suitable for cotton production based on heat unit accumulation during the growing season. For a region to be considered capable of producing cotton, total heat unit accumulation must be greater than 1000. Planting cotton earlier in the spring could allow higher lint yields, better fiber quality, and an earlier crop termination to avoid later season pests and abiotic stresses. According to Esparza et al. (2007) and Sansone et al. (2002), for every additional 41.7 heat units beyond 1000 heat units, cotton produces one more boll in non-water stressed plants.

TABLE A.1

Accumulated heat units (DD15.6s) required for different developmental stages of cotton. (Sansone et al. (2002). http://lubbocktx.tamu.edu).

| Growth Stage | Number of Days (range) | Heat Units C.° (range) |
|---|---|---|
| Planting to seedling emergence | 4-9 | 28-33 |
| Emergence to first square | 27-38 | 236-264 |
| Square to white flower2 | 0-25 | 167-194 |
| Planting to first flower | 60-70 | 431-472 |

TABLE A.1-continued

Accumulated heat units (DD15.6s) required for different developmental stages of cotton. (Sansone et al. (2002). http://lubbocktx.tamu.edu).

| Growth Stage | Number of Days (range) | Heat Units C.° (range) |
|---|---|---|
| White flower to open boll | 45-66 | 472 |
| Planting to cutout | 80-100 | 556-889 |
| Planting to harvest | 130-170 | 1,444 |
| Between nodes | | |
| Up the main stem | 2-34 | 0-33 |
| Out the branch | 5-7 | 44-67 |

Upland Cotton (*Gossypium hirsutum* L.) is believed to have originated as a product of an interspecific hybridization between the A and D genome diploid species roughly 1 to 2 million years ago (Wendel, 1989). Through many generations of natural selection and human interaction, the amount of genetic variation in cotton has become very limited. Muller (1928) used mutagenic properties of X-ray radiation to investigate the inheritance of several traits in Drosophilia flies. The use of radiation and chemically induced mutagens has been used in genetic research and has contributed to the comprehension of all of biology. Even though induced mutations in plant breeding have been a controversial subject for many years, it has been proven that mutation breeding has had a large impact in plant improvement (Larkin, 1998). Induced mutations have been very effective in creating genetic diversity, which helps breeders in developing new heritable traits previously not known within a species' genome. Marketing plant improvements without the use of transgenic approaches reduces the time and cost of releasing new cultivars.

Different mutagens have various effects on the DNA within the organism's genome. Deaminating agents remove the amine group from adenine or cytosine. Consequently during replication the altered adenine pairs with the deaminated cytosine, and cytosine to the deaminated adenine. (Brown, 2012). Intercalating agents cause deletions, reading frame shifts, or random base insertions (Brown, 2012). Ethyl methanesulfonate, or "EMS", is an alkylating agent that creates point mutations by reacting with guanine or thymine by adding an ethyl group so during DNA replication the modified base is recognized as adenine or cytosine (Balyan et al., 2008; Brown, 2012; Greene et al., 2003; McCallum et al., 2000). Greene et al. (2003) and Ashburner (1990), determined that the G/C-to-A/T occurs greater than 99% of the time, with limited chromosome breaks, which can cause aneuploidy and reduced fertility. Out of the chemical carcinogens, EMS is believed to be the most efficient mutagen for small genes (Greene et al., 2003). Another benefit of EMS is that it only changes a small number of genes resulting in mutant plants that will often maintain the adaptation of the parent cultivar which is very beneficial to the Texas High Plain's semi-arid climate (Auld et al., 1998; Auld et al., 2009).

Induced mutations have led to over 3000 released cultivars or germplasm lines around the world (FAO/IEAE, 2013). Vaidya and Young (1993) used EMS to create genetic variation in Roselle (*Hibiscus sabdariffa* L.) for traits such as dwarf, non-serrated leaf margin, chlorophyll deficiency, as well as early and late flowering, and high yielding plants. Several mutagens have successfully been used to develop desirable agronomic traits in most major crops but only occasionally in cotton (Vaidya and Young, 1993; Auld et al., 1998). Auld et al. (2007), was able to develop a high yielding cultivar with superior fiber quality compared to its parent, while maintaining adaptability to the northern regions. The biosynthetic pathway of fatty acids can be greatly influenced through chemical mutagenesis. By subjecting the allotetraploid (*Brassica napus* L.) rapeseed to a 5% v/v of EMS, Auld et al. (1992) was capable of decreasing the levels of the polyunsaturated fatty acids, linoleic (C18:2) and linolenic (C18:3), resulting in an increase in the more favorable monounsaturated fatty acid, oleic acid.

The amount of genetic diversity within the genome of upland cotton (*Gossypium hirsutum* L.), has seemed to have reached a bottleneck through millions of years of natural selection and alloploidy (Lowery et al., 2007). Induced mutations are one approach of creating genetic variation without the use of transgenes. This technology has been well established and useful for plant breeders in improving cultivars in many different species and traits (Vaidya and Young, 1993).

Cotton production in northern regions is limited by the number of heat units during the short growing season; very cool fall temperatures; and poor stand establishment. Several studies recommend a soil temperature of 18.3° C. (65° F.) at four inches for three consecutive days before planting (Boman and Lemon, 2005), which occurs around mid to late May. Since Cotton is a cold sensitive plant, it is very susceptible to the cool soil temperatures in both the early spring and fall. Clay et al., (1976) have shown that plants with lower concentrations of saturated fatty acids are more tolerant to cooler temperatures. By using a carcinogen, Ethyl Methanesulfonate (EMS) to cause a chemical mutation, the result was several cotton lines that were identified with reduced concentrations of palmitic fatty acid (C16:0), 20.2%, compared to over 26% for commercial varieties. The present disclosure provides for low palmitic lines producers will be able to plant in soils as much as 5.5° C. (10° F.) cooler, than most commercial varieties due to the high melting point of Palmitic acid, 62.8° C. (145° F.).

For the purposes of the present disclosure, the term germination refers to the growth of an embryonic plant contained within a seed; it results in the formation of the seedling. The seed of a vascular plant is a small package produced in a fruit or cone after the union of male and female sex cells. The ability of cottonseed to germinate rapidly can have a large impact on the overall yield as well as protection of the seedlings against early season pests and abiotic stresses. Many factors can reduce the ability of cotton to germinate, poor seed quality, lack of or too much water, extremes in temperatures, insects, and pathogens. Wanjura et al. (1969) evaluated the effects of plant vigor on total yield. They regressed the percent emergence at 5 days after planting to lint yield and developed a high coefficient of determination value, $r^2$=0.94.

In order for cottonseed to germinate three things must be present 1) adequate water, 2) sufficient oxygen, and 3) proper temperature (Simpson et al., 1940). Water is absorbed mainly through the chalaza region of the cotton seed, but can enter through the micropyle, the small pointed end of the seed. With sufficient moisture the chalaza end opens up allowing more rapid absorption (Simpson et al., 1940; Christiansen and Moore, 1959). Simpson et al. (1940) stated that the seed can only use oxygen once the seed has absorbed enough water, but too much water in the soil can suffocate the seed not allowing the exchange of oxygen and carbon dioxide through the seed coat. The second requirement for seed germination is adequate temperature. Ludwig (1932) stated that the minimum temperature that cotton will germinate is approximately 12° C. (55° F.), but Camp and Walker (1927) reported no germination until 14° C. (58° F.). Krzyzanowski and Delouche (2011), determined that the best temperature for cotton to germinate is between 18° to 30° C. (65° to 86° F.) with no statistical difference between these temperatures. Nonogaki et al. (2010) specified for a seed to be considered germinated the radicle must be protruding through the seed coat, which he called "visible germination".

Styles (2003), reported that after a seed has been planted, the seed will require approximately 10 to 15.6 heat units to germinate. Under the right conditions a seedling has the capability of emerging above the soil in 5-10 days after the radicle has protruded through the seed coat (2-3 days) (Oosterhuis and Jernstedt, 1999). Once these conditions have been met, the first portion of the embryo to break through the seed coat is the radicle. Nutrients in the form of starch molecules located in the cotyledons serve as a food supply until the cotyledons reach sunlight, develop chlorophyll, and begin to photosynthesize (Styles, 2003).

One other factor which impacts germination of cottonseed is the delinting process. Simpson et al. (1940) studied the effects of the seed coat on germination. In their study the compared fuzzy cotton seed against cottonseed that had been delinted with sulfuric acid. The acid-delinted seed germinated 2-3 days quicker than fuzzy cottonseed, but in the lab test there was not statistical differences by day 14. It is believed softening of the seed coat from exposure to sulfuric acid makes it more permeable to water (Ryavalad et al., 2009). They detected more of a varietal difference in germination at 14 days, than fuzzy versus acid-delinted seed treatments. Kerby et al. (1996) indicated that the lint on the fuzzy seed limits the contact with the soil limiting its ability to absorb moisture. Ryavalad et al. (2009) also determined that acid-delinted seed germinated at much higher rates than fuzzy seed after a storage period of nine months. Christidis (1936) determined that when available moisture is a limiting factor at planting, acid-delinted seed had higher germination percentages than fuzzy seed. Marani and Amirav (1970) tested the effects of acid-delinting on germinating seeds at low temperatures. They found that acid-delinted seeds had statistically higher germination rates than fuzzy seeds at 12° C. (54° F.). Both *Gossypium hirsutum* and *G. barbedence* were tested as acid-delinted and non-delinted. The effects of delinting were even observed with *G. barbedence* which does not contain as much fuzz as *G. hirsutum*. Although the correct treatments of sulfuric acid can help increase germination, a slight miscalculation on the acid percentage or the amount of time the seed is subjected to the acid can damage the seed coat resulting in poor seed germination (Ryavalad et al., 2009; Simpson et al., 1940).

The goal of a commercial cotton breeding program is to develop new, unique, and superior cotton cultivars. A breeder initially selects and crosses two or more parental lines, followed by generation advancement and selection, thus producing many new genetic combinations. For reference on general breeding techniques, see Briggs (1967), which is incorporated by reference herein in its entirety.

The first filial generation is the generation resulting immediately from a cross of the first set of parents (which are designated as the parental or P generation). The F2 generation is the result of a cross between two F1 individuals (from F1 generation). The second filial generation (F2), which is comprised of offspring(s) resulting from a cross of the members of F1 generation. Subsequent filial generations (F3, F4, F5) may result, having increased, nearly completely homogenous, or homozygous, characteristics.

Selection for desirable traits can occur at any segregating generation (F2 and above). Selection pressure is exerted on a population by growing the population in an environment where the desired trait is maximally expressed and the individuals or lines possessing the trait can be identified. For instance, selection can occur for disease resistance when the plants or lines are grown in natural or artificially-induced disease environments, and the breeder selects only those individuals having little or no disease and are thus assumed to be resistant.

It is therefore an embodiment of the present disclosure that cotton lines 2-340/1-1422, 1-1422/SCM 3-7-3, 1-1422/2-340, and 1-136/2-340 are provided herein, which are F4 cotton lines having low palmitic acid content, and are substantially homozygous genotypically and homogenous phenotypically.

Mutation breeding is the process of exposing seeds to chemicals or radiation in order to generate mutants with desirable traits to be bred with other cultivars. For the purposes of the present disclosure, plants grown from treated seeds are characterized as M1 mutants. Populations of plants grown from seeds harvested from M1 mutants are known as M2 mutants. Selection of desired mutants may start in this generation or later (M3-M8), during which continuing selection, genetic confirmation, multiplication and stabilization of field performance occurs in the mutant lines. It is therefore an embodiment of the present disclosure to provide cotton lines AFIS 1-1422 AFIS 2-340, AFIS 1-136, and SCM 3-7-3 as M5 parent mutant lines, selected for low palmitic acid content and capable of homogenous phenotypic characteristics.

In addition to phenotypic observations, the genotype of a plant can also be examined. There are many laboratory-based techniques available for the analysis, comparison, and characterization of plant genotype. Among these are Isozyme Electrophoresis, Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length polymorphisms (AFLPs), Simple Sequence Repeats (SSRs-which are also referred to as Microsatellites), and Single Nucleotide Polymorphisms (SNPs).

A transgenic or transformed plant refers to a plant which contains a recombinant polynucleotide introduced by transformation. Transformation means introducing a nucleotide sequence in a plant in any manner to cause stable or transient expression of the sequence. This may be achieved by transfection with viral vectors, transformation with plasmids, such as *Agrobacterium*-based vectors, or introduction of naked DNA by electroporation, lipofection, or particle gun acceleration or other methods known in the art. A transformed plant may refer to a whole plant as well as to seed, plant tissue, plant cells or any other plant material, and to the plant's progeny. A vector is a nucleic acid construct, generated recombinantly or synthetically, comprising nucleic acid elements that can cause expression of a gene. A donor vector is a construct for expression of a polynucleotide sequence for a transactivator gene. The transactivator gene is operably linked to a promoter. The promoter region may include tissue active-or-specific promoters, developmental stage active-or-specific promoters, inducible promoters or constitutive promoters.

The present disclosure provides a low-palmitic acid (C16:0) line selected from the group consisting of 2-340/1-1422; 1-1422/SCM 3-7-3; 1-1422/2-340; 1-136/2-340; AFIS 1-1422; AFIS 2-340; AFIS 1-136-A5, a seed sample of said cotton line having been deposited in ATCC Accession No. PTA-126033; and SCM 3-7-3, that is endogenous, and contains no genetic modification or transgene insertion. In one embodiment, the present disclosure provides a low-palmitic acid (C16:0) mutant line that is endogenous, which has a palmitic acid (C16:0) content represented as 22% of the total oil content.

In another embodiment, the present disclosure provides a low-palmitic acid (C16:0) line selected of the group consisting of 2-340/1-1422; 1-1422/SCM 3-7-3; 1-1422/2-340; 1-136/2-340; AFIS 1-1422; AFIS 2-340; AFIS 1-136-A5, a seed sample of said cotton line having been deposited in ATCC Accession No. PTA-126033; and SCM 3-7-3, that is endogenous, which has a palmitic acid (C16:0) content represented as 20% of the total oil content. In another embodiment the present disclosure provides a low-palmitic acid (C16:0) mutant line that is endogenous, which has a palmitic acid (C16:0) content represented as 17% of the total oil content of the cottonseed. In another embodiment the present disclosure provides a low-palmitic acid (C16:0) mutant line that is endogenous, which has a palmitic acid (C16:0) content represented as low as 15% of the total oil content of the cottonseed.

For the purposes of this disclosure the low palmitic acid cotton line selected from the group consisting of: 2-340/1-1422; 1-1422/SCM 3-7-3; 1-1422/2-340; 1-136/2-340; AFIS 1-1422; AFIS 2-340; AFIS 1-136-A5, a seed sample of said cotton line having been deposited in ATCC Accession No. PTA-126033; and SCM 3-7-3, is produced by conventional breeding techniques, wherein EMS is utilized for creating mutagens to display various alterations, including reduction in palmitic acid (C16:0) content, presented as a percentage of total oil content. The palmitic acid content, in one aspect of the present disclosure, is below 20% of total oil content. Mutation breeding is the process of exposing seeds to chemicals or radiation in order to generate mutants with desirable traits to be bred with other cultivars. Plants created using mutagenesis are sometimes called mutagenic plants or mutagenic seeds.

For the purposes of this disclosure, the cotton lines of the present disclosure, are identified by separate mutant genes from both the A and D genomes in cotton. The mutant genes are mutant alleles of fatb, which is a thioesterase relatively specific for palmitoylACP. When suppressed in *Arabidopsis* and soybeans, the fatb-suppressed genes have resulted in lower palmitic acid content, with potential reductions by 4% to 5% for a single mutant. The present disclosure provides for combining two separate fatb mutations which are allelic and complementary to reduce the cottonseed storage oil estimated melting point to 47° F., thus allowing for significant effect on germination and radical elongation of cotton at low temperatures (FIG. 5). Cotton fatty acid biosynthesis has been suggested to be controlled by a genetic system similar to the genetic system found in other tropical origin crops such as soybeans (Fehr, 2007).

The regulation of palmitic acid levels in cottonseed triacylglyclerols (TAGs) mostly likely will be due to mutations in enzymes of the biosynthetic pathway (FIG. 1). Like all plants, fatty acids are synthesized in developing cottonseeds in the plastid compartment in two-carbon increments by a multi-enzyme fatty acid synthase complex. Chain length terminating enzymes, the ACP thioesterases (reactions 5 and 6), release fatty acids from the plastid for export to the ER for triacylglycerol assembly. The composition of fatty acids released from plastids then is determined by the relative activity of these enzymes. In cotton a gene and cDNA encoding the palmitoylACP thioesterase (also known as fatb) were identified (Yoder et al, 1999; Pirtle, 1999) and the enzyme produced from the cDNA was confirmed to be selective for palmitoylACP (Huynh et al, 1999).

In another embodiment of the present disclosure, the present invention progeny plants are produced by crossing plants of a cotton line selected from the group contsistion of: 2-340/1-1422; 1-1422/SCM 3-7-3; 1-1422/2-340; 1-136/2-340; AFIS 1-1422; AFIS 2-340; AFIS 1-136-A5, a seed sample of said cotton line having been deposited in ATCC Accession No. PTA-126033; and SCM 3-7-3, with other, different or distinct cotton plants, and further selfing these progeny plants with other, distinct progeny plants and subsequent selection of derived progeny plants. This process may be repeated multiple times in order to produce cotton plants derived from the above-referenced cotton lines of the present disclosure.

Other than traditional breeding and mutation-based breeding, such essentially derived varieties of the cotton lines of the present disclosure may be also obtained by the selection by genetic transformation of regenerable plant tissue or cell culture by methods known in the art as further described herein. The beneficial characteristics of the cotton lines of the present disclosure may be further enhanced by other traits and characteristics, such as herbicide or pest resistance, fiber enhancements, stress tolerance, and drought tolerance.

In an embodiment of the present disclosure, a phenotypic designation of the desired characteristics utilizes the "naked seed" trait which significantly reduces the formation of linters on the surface of the cottonseed. See US Patent Application 20090055962 (Auld, et al.), incorporated by reference herein in its entirety. For the purposes of this disclosure the low palmitic oil cottonseed may be accompanied by cotton traits which provide phenotypic differentiation, such as naked-tufted seed coats. The naked seed trait has been shown to significantly enhance oil content in cottonseed (r=0.68*). The naked seed mutant also has a profound impact on lint quality. The lines carrying the naked seed mutation have reduced seed coat neps (r=−0.47*), potentially reduced short fiber content, improved yarn quality and improved AFIS fiber maturity. These are the factors which have prevented successful development of ELS (Extra Long Staple) stripper varieties in Texas.

When used in connection with the present disclosure, the naked tufted seed coats exhibit significantly reduced formation of linters on the surface of the cotton seed. In general, the lines carrying the naked seed mutation have reduced seed coat neps, reduced short fiber content, improved yarn quality, increased seed oil content, and improved AFIS fiber maturity.

In addition, the naked-tufted seed of the mutant line significantly reduces the time and energy required for ginning, oil extraction, and reduces the need to delint the cotton seed prior to planting. Thus, when used in connection with the present disclosure, the naked tufted seed would serve as a phenotypic marker for incorporation into other well-adapted commercial cultivars of upland cotton to distinguish the presence, or absence, of the low palmitic acid seeds allowing for low palmitic acid seed to be delivered to desired processing facilities, such as for cottonseed oil production, wherein the low palmitic acid benefits are desired, and to dairies, where cottonseed as a feedstock is desired to be 'fuzzy' for purposes of adding benefits to the feed. These additional traits, as incorporated into the commercial cotton cultivars, would continue to produce commercially significant quantities of commercial quality fiber.

EXAMPLES

Example 1. Emergence of Cottonseed in Cold Soils

Historically, stand establishment in the early spring is the most challenging stage of cotton production especially in cooler climates. The recent loss of Temik that was used to protect young cotton seedling from nematodes and insects has further compounded the difficulty of establishing good stands of cotton. In this study EMS was used to create a series of mutants with modest reductions in the concentration of palmitic acid from the normal of 25% to levels as low as 20 to 18%. All of the mutants selected were tested for low temperature germination and cold soil emergence. Selected lines were then intercrossed to combine genes for low palmitic acid from both the A and D genomes of tetraploid cotton to derive lines with 14 to 17% palmitic acid concentrations in the oil. These cotton lines may be able to emerge from soils at temperatures as low as 55° F.

The initial objective of the present Example was to modify the storage oils in cottonseeds to reduce the level of palmitic acid (C16:0) to approximately 20% that would allow the seedlings to emerge from cold soils (55 to 60° F.). Work was initiated to stack two low palmitic acid mutant genes in the same line to allow further reductions of palmitic acid (14 to 17%). This low level of saturated fatty acid allow cotton seedlings to rapidly emerge from very cold soils (47° to 50° F.). Both the single and double low palm mutants would improve the nutritional value of cottonseed oil in both edible oil and full fat dairy rations.

TABLE 1

Fatty acid composition, estimated seed oil melting point, germination, and root length at 59° F. of five low palmitic acid mutants, four high palmitic acid mutants, two commercial varieties and characteristics of the targeted "Double Low Palm Mutant".

| Entry | C16:0% | C18:0% | C18:1% | C18:2% | Melting Point | 59° F. Germ % | 59° F. Root Length In. |
|---|---|---|---|---|---|---|---|
| Low Palmitic (5) | 20.2 | 2.4 | 19.3 | 54.2 | 57.7 | 76 | 10.4 |
| High Palmitic (4) | 25.2 | 2.7 | 19.0 | 49.1 | 64.0 | 48 | 6.9 |
| Varieties (2) | 24.2 | 2.5 | 18.1 | 51.7 | 62.2 | 82 | 9.6 |
| Double Low Palm Mutant | 15.0 | 2.5 | 19.5 | 63.0 | 47.2 | >80 | 9-10.5 |

To test Example 1, germination studies were conducted at 50°, 55°, 60° and 65° F. on fifteen commercial varieties with approximately 25% palmitic acid and seven mutants with less than 20% palmitic acid in the seed oil to determine the impact of a single "Low Palm Allele" on seed germination and radicle growth (Tables 2 and 3). This experiment confirmed that cotton genotypes with less than 20% palmitic acid in the seed oil would have enhanced germination at temperatures below 60° F. while the conventional commercial cultivars only had good germination rates at temperatures above 600.

TABLE 2

Percent Germination of seven low palmitic mutants and 15 commercial cultivars of cotton (*Gossypium hirsutum* L.) when grown at four temperatures (50°, 55°, 60°, and 65° F.) in December of 2011. Underlined entries are low palmitic acid lines.

| Entry | 55° F. | | 60° F. | | 65° F. | |
|---|---|---|---|---|---|---|
| | Day 4 | Day 12 | Day 4 | Day 12 | Day 4 | Day 12 |
| | | | % Germination | | | |
| <u>AFIS2-340</u> | 10.7 | 34.7 | 84.0 | 96.0 | 94.7 | 98.7 |
| <u>AFIS1-136</u> | 10.7 | 25.3 | 85.3 | 96.0 | 93.3 | 98.7 |
| <u>SCM3-7-3</u> | 5.33 | 10.7 | 78.7 | 97.3 | 77.3 | 94.7 |
| <u>RM3-8-1</u> | 5.33 | 5.33 | 80.0 | 93.3 | 82.7 | 92.0 |
| <u>EM4-3-1</u> | 1.33 | 2.67 | 36.0 | 64.0 | 52.0 | 68.0 |
| <u>AFIS1-1422</u> | 1.33 | 1.33 | 74.7 | 92.0 | 84.0 | 92.0 |
| <u>SCM3-4-3</u> | 0 | 2.67 | 57.3 | 80.0 | 45.3 | 81.3 |
| DPL 0912 | 0 | 2.67 | 1.33 | 66.7 | 30.7 | 77.3 |
| FM9058 | 0 | 1.33 | 0 | 22.7 | 21.3 | 72.0 |
| PHY 499 | 0 | 1.33 | 8.00 | 84.0 | 54.7 | 96.0 |
| DPL 1044 | 0 | 1.33 | 6.67 | 92.0 | 74.7 | 92.0 |
| DPL 1032 | 0 | 1.33 | 8.00 | 81.3 | 72.0 | 86.7 |
| DPL 1133 | 0 | 0 | 13.3 | 81.3 | 74.7 | 97.3 |
| DPL 1137 | 0 | 0 | 5.33 | 74.7 | 52.0 | 88.0 |
| PHY 367 | 0 | 0 | 2.67 | 40.0 | 46.7 | 86.7 |
| PHY 375 | 0 | 0 | 21.3 | 76.0 | 64.0 | 88.0 |
| DPL 444 | 0 | 0 | 9.33 | 45.3 | 49.3 | 66.7 |
| FM 989 | 0 | 0 | 2.67 | 22.7 | 22.7 | 60.0 |
| Raider 276 | 0 | 0 | 2.67 | 45.3 | 37.3 | 89.3 |
| FM 9170 | 0 | 0 | 0 | 30.7 | 20.0 | 76.0 |
| FM 958 | 0 | 0 | 0 | 61.3 | 45.3 | 84.0 |
| Sphinx | 0 | 0 | 5.33 | 58.7 | 36.0 | 78.7 |
| CV % | 179.5 | 203.8 | 26.1 | 18.9 | 22.4 | 11.8 |
| LSD 0.05 | 4.65*** | 13.8*** | 11.4*** | 21.3*** | 20.6*** | 16.4*** |

TABLE 3

Radicle length after twelve days of seven low palmitic mutants and 15 commercial cultivars of cotton (*Gossypium hirsutum* L.) when grown at four temperatures (50°, 55°, 60°, and 65° F. in December of 2011. Underlined entries are low palm mutant lines.

| Entry | 50° F. | 55° F. | 60° F. | 65° F. |
|---|---|---|---|---|
| | | Radicle Length (mm) | | |
| <u>AFIS2-340</u> | 0 | 6.67 | 23.0 | 43.0 |
| <u>AFIS1-136</u> | 0 | 5.33 | 22.0 | 44.3 |
| <u>SCM3-7-3</u> | 0 | 3.67 | 23.3 | 62.3 |
| <u>RM3-8-1</u> | 0 | 5.33 | 30.7 | 51.0 |
| <u>EM4-3-1</u> | 0 | 5.67 | 25.3 | 52.3 |
| <u>AFIS1-1422</u> | 0 | 1.33 | 25.0 | 47.0 |
| DPL 0912 | 0 | 3.00 | 21.3 | 56.7 |
| <u>SCM3-4-3</u> | 0 | 3.00 | 24.3 | 42.7 |
| FM9058 | 0 | 1.67 | 19.7 | 39.0 |
| PHY 499 | 0 | 1.67 | 20.7 | 51.7 |
| DPL 1044 | 0 | 3.33 | 17.3 | 42.7 |
| DPL 1032 | 0 | 2.00 | 16.0 | 49.7 |
| DPL 1133 | 0 | 0 | 13.3 | 46.3 |
| DPL 1137 | 0 | 0 | 14.3 | 44.0 |
| PHY 367 | 0 | 0 | 19.0 | 44.0 |
| PHY 375 | 0 | 0 | 24.7 | 46.3 |
| DPL 444 | 0 | 0 | 20.0 | 48.7 |
| FM 989 | 0 | 0 | 19.7 | 57.0 |
| Raider 276 | 0 | 0 | 21.7 | 53.3 |
| FM 9170 | 0 | 0 | 18.0 | 47.3 |

TABLE 3-continued

Radicle length after twelve days of seven low palmitic mutants and 15 commercial cultivars of cotton (*Gossypium hirsutum* L.) when grown at four temperatures (50°, 55°, 60°, and 65° F. in December of 2011. Underlined entries are low palm mutant lines.

| Entry | 50° F. | 55° F. | 60° F. | 65° F. |
|---|---|---|---|---|
| | | Radicle Length (mm) | | |
| FM 958 | 0 | 0 | 16.7 | 51.7 |
| Sphinx | 0 | 0 | 23.7 | 42.0 |
| CV % | 0 | 123.4 | 27.6 | 12.7 |
| LSD 0.05 | 0 | 3.94** | 9.49** | 10.1** |

Figure 9:
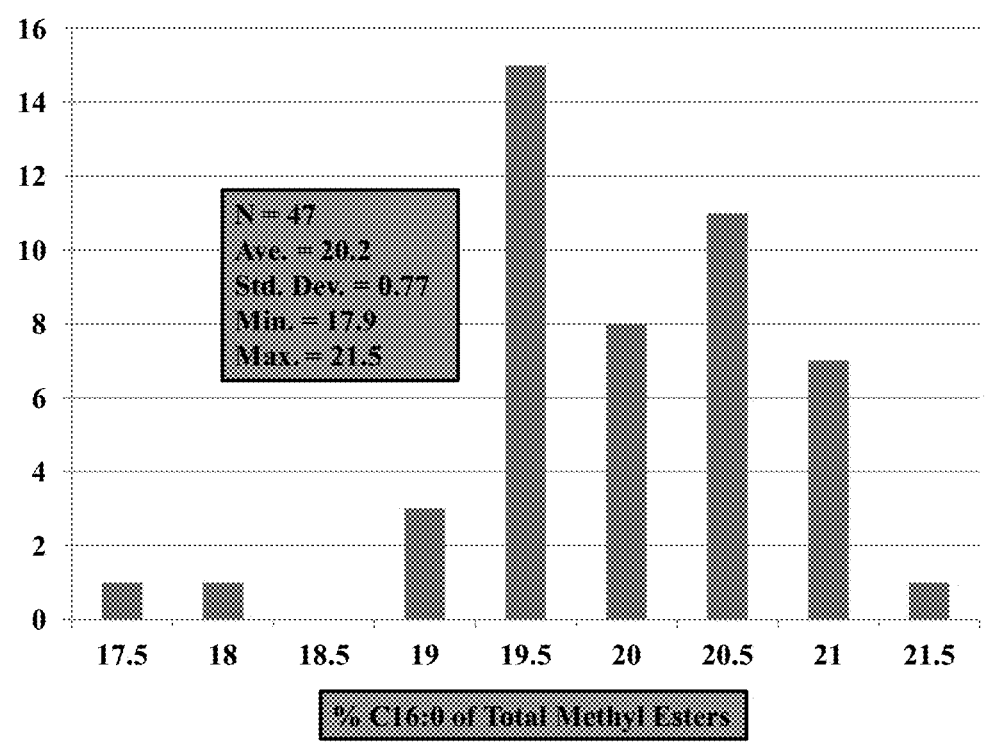
FIG. 9 depicts the distribution of palmitic acid concentration in the F2 population of AFIS2-340 -A5 X AFIS-1-1422-AI6 of cottonseed oil.
Figure 11:
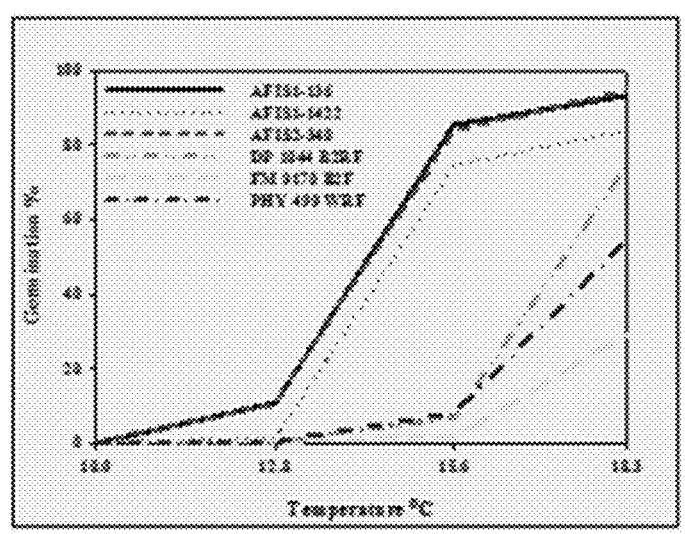
FIG. 11 depicts 4-day germination counts for various lines of cotton, including select mutant lines of the present disclosure.

A field study was then conducted in the spring of 2012 with these same mutants and again demonstrated that the single "Low Palm Allele" improved both the speed and total rate of cotton seedling establishment in cold soils under normal field conditions (Table 4). FIG. 9 shows the distribution of palmitic acid concentration in the F2 population of AFIS2-340 -A5 X AFIS-1-1422-AI6 of cottonseed oil.

TABLE 4

Percent emergence of four low palmitic mutants and 2 commercial cultivars of cotton (*Gossypium hirsutum* L.) after 14, 21, and 28 days when evaluated from May 11 to May 30 of 2012 at Lubbock, TX. Underlined entries shown are low palmitic mutants.

| Entries | 14 Days | 21 Days | 28 Days |
|---|---|---|---|
| | | % Emergence | |
| <u>SCM3-4-3</u> | 6.7 | 40.4 | 49.3 |
| <u>AFIS-1-1422</u> | 17.5 | 42.2 | 48.1 |
| <u>AFIS-1-136</u> | 10.0 | 36.1 | 42.8 |
| <u>AFIS-2-340</u> | 8.9 | 35.6 | 38.9 |
| TAM 04L-25 | 1.1 | 7.0 | 13.3 |
| Acala 1517-99 | 0.6 | 7.2 | 7.2 |

Example 2. Second Cold Germination Test

Cotton production in northern regions is limited by the lack of heat units during the short growing season; very cool fall temperatures; and poor stand establishment. The identification of a line with the ability to germinate in cool temperatures and maintain a good vigor, for quick stand establishment, would help producers on tremendously.

In 2011 cotton lines with reduced concentrations of palmitic acid were identified with levels as low as 20.2%, compared to commercial cultivars with approximately 25%. Clay et al., (1976) have shown that plants with lower concentrations of saturated fatty acids are more tolerant to cooler temperatures. These lines were tested for cool temperature germinations using germination chambers. Cotton with reduced levels of palmitic acid germinate at cooler temperatures due to the high melting point of palmitic acid, 62.8° C. (145° F.) compared to the other common fatty acids in cotton. Dowd et al. (2010) correlated the fatty acid composition from a National Cotton Variety trial. Palmitic acid proved to be negatively correlated with linoleic acid with a correlation coefficient of −0.91. Low palmitic acid would decrease the overall melting temperature since linoleic has a melting temperature of only −5° C. (23° F.). Stearic has the highest melting temperature of 69.6° C. (157.3° F.) and oleic has a melting temperature of 13.5° C. (56.3° F.). An estimated melting temperature was calculated by multiplying each percent methyl ester by its corresponding melting temperature and then summed together (Equation 2).

Cotton Oil Melting Point=Σ(([% C16:0]*62.8° C.)+
([% C18:0]*69.6° C.)+([% C18:1]*13.5° C.)+
([% C18:2]*−5° C.))  (Eq. 2)

With this Example, a germination test was conducted to test cold tolerance of 49 cotton cultivars and breeding lines. Entries included four commercial cultivars from Bayer, six commercial cultivars from Monsanto, and three commercial cultivars from Phytogen, and one cultivar, COBALT, which was the only (*Gossypium barbendence* L.) line used. Germination chambers were set to run at four constant temperatures for a total of twelve days. Temperatures were 10° C. (50° F.), 12.8° C. (55° F.), 15.6° C. (60° F.), and 18.3° C. (65° F.). The trial was arranged as a randomized split plot design with temperature being main effect and variety as the sub plot. Varieties were designed in a randomized complete block within each chamber. Each chamber contained three replications of each entry, with a total of 25 seeds of each entry per replication. Germination towels were soaked with water and seeds were spread out and rolled up. Towels were placed in aluminum trays that were positioned in the germination chambers. Germination counts were taken on day 4 and day 12. Radicle lengths were measured on day 12 to avoid breaking radicles on day 4 evaluations. A seed was considered germinated if a radicle length of at least 1 mm was obtained. Towels were rewetted prior to being placed back in chambers.

Fatty Acid composition was measured of all 31 of the 49 entries to determine lines with lower levels of palmitic acid compared with the commercially available cultivars. Samples were methylated at Texas A&M Agrilife Research & Extension Center at Lubbock, Tex. Once samples had been methylated, the fatty acid methyl esters (F.A.M.E) were analyzed using a gas chromatography (GC) at Texas Tech University.

Methylation Procedure.

Fatty acid methyl ester (F.A.M.E.) must be created for the extracted oil to be injected into the gas chromotograph (GC) for fatty acid analysis. Seeds were cut with a stainless steel razor blade on a glass plate and were cleaned in acetone prior to cutting each seed. A portion of each seed distal from the embryo axis was placed in a plastic tube for methylation. The other seed fragment containing the embryo axis was placed in another plastic tube, sealed, and placed in a freezer to be saved for future planting.

A F.A.M.E. methylation mix was made up of 29.1 ml of 14% $BF_3$ (Borontrifluoride) in MeOH (Methanol), 20.0 ml of Toluene, and lastly 50.9 ml of MeOH. Seed fragments were placed into labeled test tubes, and then 1 ml of hexane was pipetted into test tube. Seed fragments were ground using a stirring rod. The stirring rod was rinsed off inside of test tube with another ml of hexane to remove any fragments that might have stuck to the rod. The rod was cleaned with hexane between individual samples.

The top layer of oil was then pipetted out and placed into reacti-vials. The top layer was everything down to the seed fragments. The hexane was evaporated out of the reacti-vials using $N_2$ gas. Samples were placed under hood and evaporating needles lowered down into vials that were connected to the $N_2$ tank. Once evaporation was complete each vial contained a clear, solid residue.

1.5 ml of the methylation mix was added to each reacti-vial and lids were tightly secured to each vial. Reacti-vials are placed in a heating block set at 90° C. for 30 minutes under hood. At the half way point, 15 minutes, each vial is pulled out of block and shaken. At 30 minutes vials are removed and allowed to cool. Once cooled, 1.5 ml of distilled water was added into each vial, causing the sample to turn white, and poured into a large test tube. 1.5 ml of hexane was then added to each sample and vortexed to attain a clear, small bubble layer at top, whole bottom layer remained cloudy. The top layer, was pipetted off into a smaller test tube. 1.5 ml of clean hexane is then added into the large test tube containing the cloudy layer and vortexed again and then the top layer was pipetted into the small test tube once again. Small test tubes were moved to the hood to evaporate the hexane off again using the $N_2$. Once samples were dry, 1 ml of hexane was added into each test tube, the contents poured into corresponding chromatograph vials and placed in refrigerator for storage until tested.

Gas Chromatography.

An Agilent Technologies Model 6890N, Network GC system was used to analyze fatty acid methyl esters. The integration software used was the Agilent Chemstation for GC systems.

Two hexane samples were run through the column prior to beginning each set of samples. A RM-3 standard was used for calibration. The method used for analysis was an initial temperature of 200° C. for 1 minute. The temperature was then ramped at 2° C. per minute until 214° C. and held for 3 minutes. Temperature then ramped at 3° C. per minute until 230° C. and held for 10 minutes for a total run time of 26.33 minutes. Because only partial seeds were methylated the injection size was 2 μm to help concentrate the sample.

Due to the increased risk of random error in a field study a germination test was conducted in germination chambers to evaluate the relationship between cold tolerance during germination and the fatty acid composition of the cottonseed. The low palmitic lines used in the germination study were delinted seeds, which has shown to significantly increase germination at cooler temperatures (Marani and Amirav, 1970). The fatty acid compositions of all entries are included in Table 4-A.

TABLE 4.A

Estimated fatty acid composition of the seed oil of 31 genotypes of cotton used in 2011 Cold Tolerance Germination Trial. Underlined entries indicate low palm entries of the present disclosure.

| Genotype | C16:0 | C18:0 | C18:1 | C18:2 |
|---|---|---|---|---|
|  | % Methyl Ester | | | |
| AFIS1-136 | 18.3 | 2.3 | 21.6 | 57.8 |
| AFIS1-1422 | 19.9 | 2.6 | 26.5 | 51.0 |
| AFIS2-340 | 21.4 | 2.8 | 25.1 | 50.7 |
| DP 0912 B2RF | 25.7 | 2.3 | 24.5 | 47.5 |
| DP 1032 B2RF | 22.0 | 3.1 | 34.5 | 40.4 |
| DP 1044 B2RF | 24.2 | 3.1 | 25.1 | 47.6 |
| DP 1133 B2RF | 24.0 | 2.5 | 28.7 | 44.8 |
| DP 1137 B2RF | 23.6 | 3.0 | 23.2 | 50.2 |
| DP 444 BG/RR | 19.6 | 3.0 | 37.8 | 39.6 |
| EM4-3-1 | 22.9 | 2.4 | 27.4 | 47.4 |
| FM 9058F | 23.6 | 2.9 | 30.5 | 43.0 |
| FM 9170 B2F | 19.1 | 2.4 | 25.9 | 52.5 |
| FM 958 | 22.7 | 2.9 | 41.0 | 33.5 |
| FM 989 | 22.1 | 2.8 | 31.5 | 43.7 |
| Phy 367 WRF | 22.2 | 2.4 | 23.1 | 52.3 |
| Phy 375 WRF | 22.7 | 2.7 | 31.9 | 42.7 |
| Phy 499 WRF | 20.9 | 2.2 | 32.5 | 44.4 |
| Raider276 | 24.0 | 2.4 | 32.2 | 41.4 |
| RM3-8-1 | 19.8 | 2.7 | 33.4 | 44.2 |
| SCM3-4-3 | 21.9 | 2.4 | 25.2 | 50.5 |
| SCM3-7-3 | 22.2 | 2.4 | 28.5 | 46.8 |
| Sphinx | 24.6 | 2.4 | 29.4 | 43.6 |
| TTU-157-75-4 | 22.7 | 2.6 | 25.5 | 49.3 |

TABLE 4.A-continued

Estimated fatty acid composition of the seed oil of 31 genotypes of cotton used in 2011 Cold Tolerance Germination Trial. Underlined entries indicate low palm entries of the present disclosure.

| Genotype | C16:0 | C18:0 | C18:1 | C18:2 |
|---|---|---|---|---|
| | | % Methyl Ester | | |
| TTU-157-75-7 | 25.6 | 2.8 | 23.2 | 48.4 |
| TTU-157-95-1 | 25.4 | 2.6 | 21.0 | 50.9 |
| TTU-161-65-4 | 25.7 | 2.8 | 22.7 | 48.8 |
| TTU-201-35-8 | 25.4 | 2.8 | 22.0 | 49.8 |
| TTU-207-25-9 | 25.0 | 2.7 | 24.2 | 48.1 |
| TTU-207-55-5 | 24.4 | 2.6 | 25.8 | 47.2 |
| TTU-285-115-9 | 22.7 | 2.6 | 23.8 | 50.9 |
| TTU-285-125-7 | 24.8 | 2.5 | 22.1 | 50.6 |
| Average | 22.9 | 2.6 | 27.4 | 47.1 |
| Min | 18.3 | 2.2 | 21.0 | 33.5 |
| Max | 25.7 | 3.1 | 41.0 | 57.8 |
| StdDev | 2.08 | 0.231 | 4.98 | 4.76 |

Table 5 shows the mean separation of the 4 day germination counts at 12.8° C. (55° F.), 15.6° C. (60° F.), and 18.3° C. (65° F.). SAS 9.3 PROC GLM was used to calculate the coefficient of variation (CV %) and PROC GLIMMIX was used for mean separation. A square root transformation was used on all germination percentages to normalize data. There was a significant effect of temperature, cultivar, and temperature by cultivar interaction. None of the entries had begun to germinate at 10° C. (50° F.) during the four day germination counts, but AFIS2-340 and AFIS1-1422 had begun to imbibe moisture which is the initial step of seed germination. Germination counts from the 12.8° C. (55° F.) chamber did show that the 6 of the 7 low palmitic lines had germinated ranging 1.33 to 10.7%. 37 of the 49 entries had germinated by day 4 at 15.6° C. (60° F.) ranging from 1.33 to 85.3%. The low palmitic lines were statistically different from all checks at 15.6° C. (60° F.) ranging 36% to 85.3% with an LSD of 9.20. PHY 375 WRF was the nearest to the low palmitic lines with a germination percentage of 21.3%. At the highest temperature, 18.3° C. (65° F.), the top 5 lines were all low palmitic lines. DP 1133 B2RF, DP 1044 B2RF, DP 1032 B2RF, and Cobalt (*Gossypium barbedence* L.) were statistically similar to the top low palmitic lines. Germination percentage ranged from 16.0 to 94.7% at 18.3° C. (65° F.).

Day 12 had a significant temperature by cultivar interaction (Table 6). By day 12 no lines had germinated at 10° C. (50° F.) but the radicle on a few of the low palmitic lines had begun to protrude the micropyle region of the seed. At 12.8° C. (55° F.) 14 of the entries had germination percentages ranging from 1.33 to 34.7%. With a LSD (0.05) of 8.9%, two of the low palmitic lines, AFIS2-340 and AFIS1-136 were statistically different from all other lines. All entries had germinated by day 12 at 15.6° C. (60° F.) ranging 22.7 to 96%. The top LSD grouping contained all of the low palmitic lines except for EM4-3-1, as well as the commercial cultivars DP1044 B2RF, PHY 499 WRF, DP 1032 B2RF, DP 1133 B2RF, and the (*Gossypium barbedence* L.) line, COBALT. 23 of the 49 lines fell within the top LSD grouping at 18.3° C. (65° F.) which included all of the low palmitic lines again except for EM4-3-1. Range of germination percentage at the highest temperature was from 60 to 98%.

Table 7 contains the mean separation of the radicle length (mm) 12 days after inhibition. The radicle length of the 14 lines that had germinated at 12.8° C. (55° F.) ranged 1.33 to 6.34 mm. The top LSD again contained the 5 low palmitic lines that had germinated ranging 3.67 to 6.34 mm. At 15.6° C. (60° F.) the radicle length ranged 13.4 to 30.8 mm with COBALT having the longest radicle. At 18.3° C. (65° F.), COBALT was statistically different from all other entries with a radicle length of 80.5 mm. The range at the highest temperature was 39.2 to 80.5 mm.

TABLE 5

Mean percent germination of 49 genotypes of cotton after 4 days of inhibition at three temperatures. Underlined entries indicate low palm entries of the present disclosure.

| Entry | Trait | 12.8° C. (55° F.) | 15.6° C. (60° F.) | 18.3° C. (65° F.) |
|---|---|---|---|---|
| | | % Germination | | |
| AFIS1-136 | LP | 10.7† | 85.3† | 93.3† |
| AFIS2-340 | LP | 10.7 | 84.0 | 94.7 |
| RM3-8-1 | LP | 5.33 | 80.0 | 82.7 |
| SCM3-7-3 | LP | 5.33 | 78.7 | 77.3 |
| AFIS1-1422 | LP | 1.33 | 74.7 | 84.0 |
| EM4-3-1 | LP | 1.33 | 36.0 | 52.0 |
| Atlas | CK | 0.00 | 1.33 | 54.7 |
| Atlas11-5-3S-3 | HO | 0.00 | 0.00 | 20.0 |
| Atlas11-5-3S-8 | HO | 0.00 | 0.00 | 30.7 |
| Atlas11-5-3S-9 | HO | 0.00 | 0.00 | 37.3 |
| Atlas185-6-2S-2 | HO | 0.00 | 4.00 | 56.0 |
| Cobalt | CC | 0.00 | 1.33 | 72.0 |
| DP 0912 B2RF | CC | 0.00 | 1.33 | 30.7 |
| DP 1032 B2RF | CC | 0.00 | 8.00 | 72.0 |
| DP 1044 B2RF | CC | 0.00 | 6.67 | 74.7 |
| DP 1133 B2RF | CC | 0.00 | 13.3 | 74.7 |
| DP 1137 B2RF | CC | 0.00 | 5.33 | 52.0 |
| DP 444 BG/RR | CC | 0.00 | 9.33 | 49.3 |
| Explorer | CK | 0.00 | 2.67 | 36.0 |
| Explorer 162-5-3S-4 | HO | 0.00 | 0.00 | 49.3 |
| FM 9058F | CC | 0.00 | 0.00 | 21.3 |
| FM 9170 B2F | CC | 0.00 | 1.33 | 29.3 |
| FM 958 | CC | 0.00 | 3.33 | 40.7 |
| FM 989 | CC | 0.00 | 2.67 | 22.7 |
| Hol338P40-4-3S-4 | CC | 0.00 | 2.67 | 33.3 |
| Hol338P40-5-2S-2 | HO | 0.00 | 5.33 | 28.0 |
| Hol338P40-5-3S-1 | HO | 0.00 | 0.00 | 18.7 |
| Hol338P40-5-3S-4 | HO | 0.00 | 0.00 | 28.0 |
| Hol338P40-5-3S-5 | HO | 0.00 | 0.00 | 36.0 |
| Hol338P89-3-3S-9 | HO | 0.00 | 2.67 | 44.0 |
| Holland338 | CK | 0.00 | 12.0 | 61.3 |
| Phy 367 WRF | CC | 0.00 | 2.67 | 46.7 |
| Phy 375 WRF | CC | 0.00 | 21.3 | 64.0 |
| Phy 499 WRF | CC | 0.00 | 8.00 | 54.7 |
| Raider276 | CK | 0.00 | 2.67 | 37.3 |
| SC9023 | CK | 0.00 | 4.00 | 49.3 |
| SC9023P208-1-1S-7 | HO | 0.00 | 1.33 | 25.3 |
| SCM3-4-3 | LP | 0.00 | 57.3 | 45.3 |
| Sphinx | CK | 0.00 | 5.33 | 36.0 |
| Sphinx 86-4-3S-2 | HO | 0.00 | 2.67 | 16.0 |
| TTU-157-75-4 | SLP | 0.00 | 4.00 | 46.7 |
| TTU-157-75-7 | SLP | 0.00 | 0.00 | 45.3 |
| TTU-157-95-1 | SLP | 0.00 | 9.33 | 26.7 |
| TTU-161-65-4 | SLP | 0.00 | 0.00 | 29.3 |
| TTU-201-35-8 | SLP | 0.00 | 0.00 | 46.7 |
| TTU-207-25-9 | SLP | 0.00 | 1.33 | 32.0 |
| TTU-207-55-5 | SLP | 0.00 | 6.67 | 45.3 |
| TTU-285-115-9 | SLP | 0.00 | 0.00 | 44.0 |
| TTU-285-125-7 | SLP | 0.00 | 9.33 | 60.0 |
| LSD (0.05) - Entry | | 2.98 | 9.20 | 24.1 |
| CV % - Entry | | 220.0 | 45.7 | 34.6 |
| LSD (0.05) - Entry * Temp | | 15.2 | | |
| CV % - Entry * Temp | | 36.6 | | |
| Significance - Entry | | <0.0001 | | |
| Significance - Temp | | <0.0001 | | |
| Significance - Entry * Temp | | <0.0001 | | |

LP—Low Palmitic Mutant
CK—Conventional Check
CC—Commercial Cultivar
HO—High Oil Mutant
SLP—Segregating Low Palmitic Mutant
†Means different by more than the Entry LSD value differ at the 0.05 probability level in each column, and more than the Entry * Temp LSD value in each Row or Column by Fisher's Protected Least Significant Difference

TABLE 6

Mean percent germination of 49 genotypes of cotton after 12 days of inhibition at three temperatures. Underlined entries indicate low palm entries of the present disclosure.

| Entry | Trait | 12.8° C. (55° F.) | 15.6° C. (60° F.) | 18.3° C. (65° F.) |
|---|---|---|---|---|
| | | | % Germination | |
| AFIS2-340 | LP | 34.7 | 96.0 | 98.7 |
| AFIS1-136 | LP | 25.3 | 96.0 | 98.7 |
| SCM3-7-3 | LP | 10.7 | 97.3 | 94.7 |
| RM3-8-1 | LP | 5.33 | 93.3 | 92 |
| DP 0912 B2RF | CC | 2.67 | 66.7 | 77.3 |
| EM4-3-1 | LP | 2.67 | 64.0 | 68 |
| SCM3-4-3 | LP | 2.67 | 80.0 | 81.3 |
| AFIS1-1422 | LP | 1.33 | 92.0 | 92 |
| DP 1032 B2RF | CC | 1.33 | 81.3 | 86.7 |
| DP 1044 B2RF | CC | 1.33 | 92.0 | 92 |
| FM 9058F | CC | 1.33 | 22.7 | 72 |
| Hol338P89-3-3S-9 | HO | 1.33 | 52.0 | 84 |
| PHY 499 WRF | CC | 1.33 | 84.0 | 96 |
| TTU-285-125-7 | SLP | 1.33 | 72.0 | 86.7 |
| Atlas | CK | 0.00 | 62.7 | 89.3 |
| Atlas11-5-3S-3 | HO | 0.00 | 25.3 | 72 |
| Atlas11-5-3S-8 | HO | 0.00 | 48.0 | 77.3 |
| Atlas11-5-3S-9 | HO | 0.00 | 56.0 | 82.7 |
| Atlas185-6-2S-2 | HO | 0.00 | 66.7 | 92 |
| Cobalt | CC | 0.00 | 78.7 | 88 |
| DP 1133 B2RF | CC | 0.00 | 81.3 | 97.3 |
| DP 1137 B2RF | CC | 0.00 | 74.7 | 88 |
| DP 444 BG/RR | CC | 0.00 | 45.3 | 66.7 |
| Explorer | CK | 0.00 | 44.0 | 81.3 |
| Explorer 162-5-3S-4 | HO | 0.00 | 74.7 | 94.7 |
| FM 9170 B2F | CC | 0.00 | 52.0 | 80 |
| FM 958 | CC | 0.00 | 48.0 | 78.7 |
| FM 989 | CC | 0.00 | 22.7 | 60 |
| Hol338P40-4-3S-4 | HO | 0.00 | 44.0 | 72 |
| Hol338P40-5-2S-2 | HO | 0.00 | 32.0 | 70.7 |
| Hol338P40-5-3S-1 | HO | 0.00 | 46.7 | 66.7 |
| Hol338P40-5-3S-4 | HO | 0.00 | 42.7 | 72 |
| Hol338P40-5-3S-5 | HO | 0.00 | 64.0 | 89.3 |
| Holland338 | CK | 0.00 | 68.0 | 82.7 |
| PHY 367 WRF | CC | 0.00 | 40.0 | 86.7 |
| PHY 375 WRF | CC | 0.00 | 76.0 | 88 |
| Raider276 | CK | 0.00 | 45.3 | 89.3 |
| SC9023 | CK | 0.00 | 64.0 | 88 |
| SC9023P208-1-1S-7 | HO | 0.00 | 54.7 | 74.7 |
| Sphinx | CK | 0.00 | 58.7 | 78.7 |
| Sphinx 86-4-3S-2 | HO | 0.00 | 37.3 | 69.3 |
| TTU-157-75-4 | SLP | 0.00 | 65.3 | 81.3 |
| TTU-157-75-7 | SLP | 0.00 | 53.3 | 89.3 |
| TTU-157-95-1 | SLP | 0.00 | 68.0 | 82.7 |
| TTU-161-65-4 | SLP | 0.00 | 46.7 | 86.7 |
| TTU-201-35-8 | SLP | 0.00 | 60.0 | 90.7 |
| TTU-207-25-9 | SLP | 0.00 | 41.3 | 81.3 |
| TTU-207-55-5 | SLP | 0.00 | 61.3 | 85.3 |
| TTU-285-115-9 | SLP | 0.00 | 65.3 | 84 |
| LSD (0.05) - Entry | | 8.9 | 21.3 | 13.0 |
| CV % - Entry | | 182.7 | 24.1 | 10.7 |
| LSD (0.05) - Entry * Temp | | 15.5 | | |
| CV % Entry * Temp | | 14.9 | | |
| Significance - Entry | | <0.0001 | | |
| Significance - Temp | | <0.0001 | | |
| Significance - Entry * Temp | | <0.0001 | | |

† Means different by more than the Entry LSD value differ at the 0.05 probability level in each column, and more than the Entry * Temp LSD value in each Row or Column by Fisher's Protected Least Significant Difference

TABLE 7

Mean radicle length of 49 genotypes of cotton after 12 days of inhibition at three temperatures. Underlined entries indicate low palm entries of the present disclosure.

| Entry | Trait | 12.8° C. (55° F.) | 15.6° C. (60° F.) | 18.3° C. (65° F.) |
|---|---|---|---|---|
| | | | Radicle Length (mm) | |
| AFIS1-136 | LP | 5.51 | 21.9 | 44.4 |
| AFIS1-1422 | LP | 1.33 | 25.0 | 46.7 |
| AFIS2-340 | LP | 6.34 | 23.2 | 43.2 |
| Atlas | CK | 0 | 16.2 | 49.8 |
| Atlas11-5-3S-3 | HO | 0 | 17.8 | 51.6 |
| Atlas11-5-3S-8 | HO | 0 | 20.2 | 48.4 |
| Atlas11-5-3S-9 | HO | 0 | 22.2 | 56.3 |
| Atlas185-6-2S-2 | HO | 0 | 21.4 | 61.0 |
| Cobalt | CC | 0 | 30.8 | 80.5 |
| DP 0912 B2RF | CC | 3.14 | 21.4 | 56.7 |
| DP 1032 B2RF | CC | 2.04 | 15.9 | 49.6 |
| DP 1044 B2RF | CC | 3.23 | 17.3 | 42.9 |
| DP 1133 B2RF | CC | 0 | 13.4 | 46.5 |
| DP 1137 B2RF | CC | 0 | 14.3 | 44.0 |
| DP 444 BG/RR | CC | 0 | 20.0 | 48.7 |
| EM4-3-1 | LP | 5.56 | 25.1 | 52.6 |
| Explorer | CK | 0 | 17.1 | 49.1 |
| Explorer 162-5-3S-4 | HO | 0 | 17.9 | 50.4 |
| FM 9058F | CC | 1.83 | 19.7 | 39.2 |
| FM 9170 B2F | CC | 0 | 21.9 | 52.9 |
| FM 958 | CC | 0 | 20.5 | 49.6 |
| FM 989 | CC | 0 | 19.5 | 57.2 |
| Hol338P40-4-3S-4 | HO | 0 | 15.7 | 52.8 |
| Hol338P40-5-2S-2 | HO | 0 | 20.8 | 43.6 |
| Hol338P40-5-3S-1 | HO | 0 | 19.2 | 51.2 |
| Hol338P40-5-3S-4 | HO | 0 | 18.9 | 55.6 |
| Hol338P40-5-3S-5 | HO | 0 | 21.3 | 55.2 |
| Hol338P89-3-3S-9 | HO | 2.2 | 19.3 | 45.0 |
| Holland338 | CK | 0 | 25.7 | 51.6 |
| PHY 367 WRF | CC | 0 | 18.9 | 44.0 |
| PHY 375 WRF | CC | 0 | 24.6 | 46.4 |
| PHY 499 WRF | CC | 1.67 | 20.6 | 51.3 |
| Raider276 | CK | 0 | 21.8 | 53.1 |
| RM3-8-1 | LP | 5.33 | 30.4 | 50.8 |
| SC9023 | CK | 0 | 23.5 | 55.4 |
| SC9023P208-1-1S-7 | HO | 0 | 21.4 | 51.9 |
| SCM3-4-3 | LP | 3.04 | 24.3 | 42.6 |
| SCM3-7-3 | LP | 3.67 | 23.4 | 62.3 |
| Sphinx | CK | 0 | 23.8 | 41.7 |
| Sphinx 86-4-3S-2 | HO | 0 | 17.7 | 47.5 |
| TTU-157-75-4 | SLP | 0 | 26.0 | 56.1 |
| TTU-157-75-7 | SLP | 0 | 17.3 | 52.6 |
| TTU-157-95-1 | SLP | 0 | 19.6 | 51.8 |
| TTU-161-65-4 | SLP | 0 | 19.1 | 49.4 |
| TTU-201-35-8 | SLP | 0 | 20.4 | 49.8 |
| TTU-207-25-9 | SLP | 0 | 19.2 | 50.5 |
| TTU-207-55-5 | SLP | 0 | 23.5 | 55.8 |
| TTU-285-115-9 | SLP | 0 | 28.7 | 55.8 |
| TTU-285-125-7 | SLP | 1.67 | 25.4 | 51.1 |
| LSD (0.05) - Entry | | 2.74 | 7.11 | 10.5 |
| CV % - Entry | | 14.9 | | |
| LSD (0.05) - Entry * Temp | | 7.81 | | |
| CV % - Entry * Temp | | 177.3 | 27.2 | 14.0 |
| Entry | | <0.0001 | | |
| Temp | | <0.0001 | | |
| Entry * Temp | | <0.0001 | | |

† Means different by more than the Entry LSD value differ at the 0.05 probability level in each column, and more than the Entry * Temp LSD value in each Row or Column by Fisher's Protected Least Significant Difference Example 3: Regression Analysis A regression model was calculated using SAS 9.3 PROC REG. The day 4 germination counts were used as the dependent variable and regressed against each fatty acid. The square root was taken of germination counts again to normalize data to avoid a false high $r^2$ value.

At 12.8° C. (55° F.) palmitic had a coefficient of determination ($r^2$) of 0.19 which was significant at the 0.05 level. A significance level of 0.10 is included due to the increased risk of a Type II error in which there is a difference, but the difference couldn't quite overcome the experimental error and was designated in the regression tables with a symbol (†). Table 8 contains these results. Linoleic acid was significant at the 0.10 level with an $r^2$ value of 0.12. The calculated estimated melting temperature, which took all fatty acids into account, had the highest value, $r^2=0.35^{**}$. Variables stearic and oleic neither were statistically correlated to 4 day germination counts at 12.8° C. (55° F.). The only variables that were statistically significant at 15.6° C. (60° F.) were palmitic and estimated melting temperature with $r^2$ values of 0.21 and 0.33, respectively. At 18.3° C. (65° F.) only palmitic and estimated melting temperature were correlated with germination percentage, both at the 0.10 level with $r'^2$ values of 0.12.

TABLE 8

Regression formulas to predict 4-day germination percentage of 31 cotton genotypes at three temperatures.

| Temperature ° C. | Independent Variable | Empirical Model | $r^2$ |
|---|---|---|---|
| 12.8° C. | C16:0 | y = 0.462 − 0.018x | 0.19* |
| (55° F.) | C18:0 | y = 0.278 − 0.089x | 0.04 ns |
|  | C18:1 | y = 0.101 − 0.002x | 0.01 ns |
|  | C18:2 | y = 0.007x − 0.267 | 0.12† |
|  | Estimated Melt. Temp. | y = 14.7 − 0.220x | 0.35** |
| 15.6° C. | C16:0 | y = 1.70 − 0.061x | 0.21* |
| (60° F.) | C18:0 | y = 1.30 − 0.369x | 0.08 ns |
|  | C18:1 | y = 0.419 − 0.003x | 0.00 ns |
|  | C18:2 | y = 0.018x − 0.502 | 0.08 ns |
|  | Estimated Melt. Temp. | y = 46.8 − 0.670x | 0.33** |
| 18.3° C. | C16:0 | y = 12.2 − 0.225x | 0.12† |
| (65° F.) | C18:0 | y = 0.190x + 6.55 | 0.00 ns |
|  | C18:1 | y = 0.007x + 6.85 | 0.00 ns |
|  | C18:2 | y = 0.037x + 5.33 | 0.02 ns |
|  | Estimated Melt. Temp. | y = 19.8 − 0.196x | 0.12† | y = square root of germination percentage

Table 9 contains the regression results from the day 12 germination counts. At 12.8° C. (55° F.) palmitic, linoleic, and estimated germination were the only variables that were statistically correlated to germination percentages with $r^2$ values of 0.12, 0.14, and 0.29 respectively. No variable was considered statistically correlated to germination counts at 15.6° C. (60° F.) or 18.3° C. (65° F.).

The radicle length (mm) was also used as a dependent variable and regressed against each fatty acid (Table 10). Due to many entries not germinating at 12.8° C. (55° F.) the square root was taken of the radicle length to normalize the data and also due to the wide range at 15.6° C. (60° F.). At 12.8° C. (55° F.) the only variable that was correlated to radicle length was the estimated melting temperature with a $r^2$ value of 0.16, and was significant at the 0.05 level. Stearic and germination temperature was correlated at 15.6° C. (60° F.) with 12 values of 0.20 and 0.11 respectively. Stearic was significant at the 0.05 level and estimated melting temperature at 0.10. No variable was considered statistically significant at 18.3° C. (65° F.).

TABLE 9

Regression formulas to predict 12-day germination percentage of 31 cotton genotypes at three temperatures.

| Temperature ° C. | Independent Variable | Empirical Model | $r^2$ |
|---|---|---|---|
| 12.8° C. | C16:0 | y = 0.594 − 0.022x | 0.12† |
| (55° F.) | C18:0 | y = 0.448 − 0.135x | 0.04 ns |
|  | C18:1 | y = 0.219 − 0.005x | 0.03 ns |
|  | C18:2 | y = 0.011x − 0.409 | 0.14* |
|  | Estimated Melt. Temp. | y = 20.7 − 0.304x | 0.29** |
| 15.6° C. | C16:0 | y = 0.919 − 0.005x | 0.01 ns |
| (60° F.) | C18:0 | y = 1.12 − 0.122x | 0.04 ns |
|  | C18:1 | y = 0.952 − 0.005x | 0.05 ns |
|  | C18:2 | y = 0.008x + 0.406 | 0.09 ns |
|  | Estimated Melt. Temp. | y = 18.5 − 0.161x | 0.09 ns |
| 18.3° C. | C16:0 | y = 9.42 − 0.009x | 0.00 ns |
| (65° F.) | C18:0 | y = 9.85 − 0.245x | 0.01 ns |
|  | C18:1 | y = 9.66 − 0.016x | 0.03 ns |
|  | C18:2 | y = 0.023x + 8.10 | 0.05 ns |
|  | Estimated Melt. Temp. | y = 11.9 − 0.041x | 0.04 ns | y = square root of germination percentage

TABLE 10

Regression formulas to predict 12-day radicle length of 31 genotypes of cotton at three temperatures.

| Temperature ° C. | Independent Variable | Empirical Model | $r^2$ |
|---|---|---|---|
| 12.8° C. | C16:0 | y = 3.17 − 0.107x | 0.07 ns |
| (55° F.) | C18:0 | y = 3.05 − 0.869x | 0.05 ns |
|  | C18:1 | y = 1.31 − 0.020x | 0.01 ns |
|  | C18:2 | y = 0.050x − 1.55 | 0.07 ns |
|  | Estimated Melt. Temp. | y = 10.2 − 0.145x | 0.16* |
| 15.6° C. | C16:0 | y = 5.27 − 0.030x | 0.03 ns |
| (60° F.) | C18:0 | y = 6.81 − 0.841x | 0.20* |
|  | C18:1 | y = 4.86 − 0.010x | 0.02 ns |
|  | C18:2 | y = 0.020x + 3.63 | 0.06 ns |
|  | Estimated Melt. Temp. | y = 8.12 − 0.054x | 0.11† |
| 18.3° C. | C16:0 | y = 0.510x + 38.0 | 0.05 ns |
| (65° F.) | C18:0 | y = 67.4 − 6.76x | 0.09 ns |
|  | C18:1 | y = 51.3 − 0.063x | 0.00 ns |
|  | C18:2 | y = 50.0 − 0.011x | 0.00 ns |
|  | Estimated Melt. Temp. | y = 0.296x + 30.3 | 0.02 ns |

12.8° C. and 15.6° C.; y = square root of radicle length (mm)
18.3° C.; y = radicle length (mm)

The objective of this Example was to determine the correlation between cold tolerance during germination and the fatty acid composition of cotton lines. Mean germination showed the low palmitic lines began to germinate quicker and at cooler temperatures, which would be very beneficial for producers. Bolek (2010) stated that cotton's ability to establish a stand of vigorous seedlings is a key component in the production of cotton in areas experiencing cool temperatures during the early seedling stages. Some variation in this study could have been due to the low palmitic seeds being delinted and harvested in a different environment. At the higher temperatures, 15.6° C. (60° F.) and 18.3° C. (65° F.), on day 12 several of the fuzzy seeds were statistically equivalent to the low palmitic acid lines. PHY 499 WRF which did contain lower levels of palmitic acid than most of the commercial cultivars was in the top LSD grouping at 15.6° C. (60° F.) and 18.3° C. (65° F.) at day 12.

From the 4 day regressions it was concluded that palmitic acid was the largest single variable influencing on germination, besides estimated melting point, but this takes all four fatty acids into consideration. Stroller and Weber (1975) explained that tissues with lower quantities of saturated fatty acids would be more cold tolerant and have lower freezing points.

No single variable was considered significantly correlated to radicle length at 12.8° C. (55° F.). Estimated melting temperature was considered statistically correlated to radicle length. At 15.6° C. (60° F.) stearic was the only single variable that was significantly correlated to radicle length. Stearic had the lowest standard deviation of all the fatty acids in the germination study, but could potentially have the largest impact on cold tolerance since it has the highest melting temperature of 69.6° C. (157.3° F.). No variable was significantly correlated to radicle length at the highest temperature of 18.3° C. (65° F.).

From these results a conclusion can be made that germination percentage is greatly influenced by fatty acid composition, but further clarifies that such composition requires low palmitic acid percentages.

Example 4. Segregating Populations Derived from Crossing Multiple Low Palmitic Parents The results from the previous Examples indicate that with a slight reduction in palmitic acid, germination occurs quicker as well as at cooler temperatures. The identification of lines with a further reduction in palmitic acid could potentially lead to cotton varieties that germinate at temperatures below 12.8° C. (55° F.). Induced mutations have been proven to be an effective tool in creating genetic diversity helping breeders in developing new heritable traits not previously known within a specie's genome. The chemical carcinogen, ethyl methanesulfonate (EMS) has been used in altering the biosynthetic pathway in many plant species. By subjecting cotton to EMS, mutant varieties have been identified with concentrations of palmitic acid as low as 15% compared to over 25% in commercial cultivars.

Cotton breeders have historically planted experimental trials earlier in the season to screen for cold tolerance by evaluating plots for uniform stands and for vigor (Hall, 2003). An alternative screening process would be beneficial to breeders. The objective of this Example 3 was to evaluate mutant genotypes for lower concentrations of palmitic acid and cross these lines to screen the segregating population for further reductions in C16:0.

Crossing of Low Palmitic Lines

Two cultivars were treated with a 3% v/v of Ethyl Methanosulfonate (EMS). Chemical mutagenesis has been shown to be an ideal tool for manipulating fatty acid composition in higher plants (Auld et al., 1992). The two cultivars, TAM 94L-25 (AFIS1) and Acala 1517-99 (AFIS2), were selected due to their superior fiber quality (Cantrell, et al., 2000; Smith, 2003). These lines were part of a divergent fiber quality trail from selections that were made in 2006. Fatty acid compositions, multiple seeds, of 7 mutant genotypes were tested using gas chromatography for reduced concentrations of palmitic fatty acid (C16:0). A half seed approach was used, so if a seed came back with reduced palmitic the half containing the embryo could be planted. The remaining half was cut and ground for fatty acid analysis. In the spring of 2011, lines with a reduction in palmitic were grown in the greenhouse and used as parents for low palmitic×low palmitic crosses (Table 11). A total of twelve crosses were harvested. Approximately 5 $F_1$ seeds per cross, for a total of 60 seeds, were planted and selfed over the winter. $F_2$ seeds were harvested from individual plants for GC analysis.

TABLE 11

Estimated fatty acid composition of 11 Parental lines used for low palm/low palm crosses.

| Parent | C16:0 | C18:0 | C18:1 | C18:2 |
|---|---|---|---|---|
| | | % Methyl Ester | | |
| AFIS1-136-A1 | 18.1 | 2.0 | 15.8 | 61.8 |
| AFIS1-136-A12 | 18.2 | 2.2 | 15.1 | 62.3 |
| AFIS1-136-A16 | 17.9 | 2.2 | 15.7 | 62.1 |
| AFIS1-136-A5 | 18.2 | 2.3 | 16.7 | 60.6 |
| AFIS1-1422-A16 | 19.7 | 2.2 | 18.0 | 57.1 |
| AFIS1-1422-A5 | 18.1 | 2.7 | 18.0 | 58.7 |
| AFIS2-340-A5 | 18.2 | 2.2 | 18.7 | 58.1 |
| AFIS2-340-A7 | 18.8 | 1.9 | 16.0 | 60.2 |
| AFIS2-340-A8 | 18.6 | 2.4 | 17.7 | 58.3 |
| AFIS2-340-A20 | 19.0 | 2.3 | 17.7 | 58.4 |
| SCM3-7-3-A3 | 18.7 | 1.9 | 20.0 | 56.8 |

Screening of Previously Identified TTU Low Palmitic Lines

Within the previous Examples nine genotypes were included that were previously identified as low palmitic mutants in 1995. Individual lines were screened by analyzing the fatty acid composition of multiple half seeds per genotype to see if any lines had maintained the low palmitic traits through the years of outcrossing. Since the lines were suspected of outcrossing half seeds analysis of individuals was used to screen for the low palmitic trait.

Crossing of Low Palmitic Lines

Fatty acid composition of 7 of the $F_1$ progeny from the low palmitic×low palmitic crosses was analyzed using gas chromatography (Table 12). It was hypothesized that the $F_1$ seeds would contain higher levels of palmitic acid than either of the parents (over dominance gene action) and would segregate in the $F_2$ generation in 15:1 phenotypic ratio (high C16:0):(low C16:0). All $F_1$ seeds analyzed contained a higher concentration of C16:0 than either of its parents. Cross 2-340-A5/1-1422-A16 had an increase of 6.5% in palmitic acid from its higher palmitic acid parent, 1-1422-A16, which had a concentration of 19.7%.

Fatty acid composition was analyzed on a total of 547 $F_2$ half seeds from nine crosses (Table 13). 25 seeds were analyzed from the cross 1-1422-A16/1-136-A1 with 2 of the seeds containing a concentration of C16:0 less than 18.5% which is one standard deviation away from the mean 19.5%. 1-1422-A5/2-340-A7 had a total of 68 seeds from 3 plants analyzed for fatty acid composition. Plant 2 and 3 contained a total of 4 seeds with levels of palmitic acid less than 18.5% with plant 3 containing a seed with a palmitic acid concentration as low as 17.3% which is two standard deviations away from the mean 22.1%. The most productive cross 1-1422-A5/SCM3-7-3-A3 which contained a total of 23 seeds with a palmitic acid concentration lower than 18.5% out of a total of 121 seeds. All but one of the plants analyzed contained the lower levels. This cross contained 4 seeds that contained palmitic acid concentrations that were one standard deviation away from the mean 19.5%. Plant 1 and 2 both contained seeds with levels of C16:0 as low as 17.2%. One of the three plants analyzed for cross 2-340-A5/1-1422-A16 contained 2 seeds with palmitic acid levels less than 18.5% with one seed as low as 17.9%. Both seeds from plant 1 were two standard deviations away from the mean. Lastly cross 2-340-A5/1-1422-A5 contained a total of 10 out of 42 seeds, 1 out of 2 plants, with concentrations of C16:0 lower than 18.5%. Plant 3 contained a seed with levels as low as 17.8% and 3 seeds that were one standard deviation away from the mean of 18.7%. With the reduced levels of palmitic acid the lines simultaneously had an increase in either oleic or linoleic acid.

Pearson correlation coefficient was computed using SAS Enterprise Guide 5.1 PROC CORR. Correlation coefficient (r) was calculated to identify the relationship between the fatty acids of the segregating populations (Table 14). Palmitic acid had a negative correlation with oleic and linoleic acid with r=−0.30* and −0.16 respectively. Stearic also had a negative correlation with linoleic acid with r=−0.24*. Oleic and linoleic had a high negative correlation with r=−0.84*.

TABLE 12

Fatty acid composition of a single F1 seed for 7 crosses between 9 low palmitic acid lines.

| Pedigree | C16:0 $P_1$ | C16:0 $P_2$ | C16:0 | C18:0 | C18:1 | C18:2 |
|---|---|---|---|---|---|---|
| | | | % Methyl Ester | | | |
| 1-136-A5 × 2-340-A20 | 18.2 | 19.0 | 24.3 | 2.4 | 23.0 | 50.4 |
| 1-136-A5 × 2-340-A7 | 18.2 | 18.8 | 21.8 | 2.4 | 20.1 | 55.7 |
| 1-1422-A16 × 1-136-A1 | 19.7 | 18.1 | 22.5 | 2.5 | 21.8 | 53.2 |
| 1-1422-A16 × 1-136-A12 | 19.7 | 18.2 | 21.7 | 2.4 | 25.1 | 50.9 |
| 1-1422-A5 × 2-340-A8 | 18.1 | 18.6 | 21.3 | 2.1 | 18.0 | 58.6 |
| 2-340-A5 × 1-136-A5 | 18.2 | 18.2 | 23.2 | 2.2 | 19.0 | 55.5 |
| 2-340-A5 × 1-1422-A16 | 18.2 | 19.7 | 26.2 | 3.7 | 20.7 | 49.4 |

TABLE 13

Percent palmitic acid concentration of 547 F2 seeds derived from nine crosses.

| Pedigree | Plant No. | Count | Mean | STD | Range | <18.5% |
|---|---|---|---|---|---|---|
| 1-136-A5/ 1-1422-A5 | 2 | 24 | 20.8 | 0.75 | 19.6-22.3 | 0 |
| 1-136-A5/ 2-340-A7 | | 71 | 20.1 | 0.60 | 19.0-21.9 | 0 |
| | 1 | 48 | 20.2 | 0.61 | 19.1-21.9 | 0 |
| | 3 | 23 | 19.9 | 0.55 | 19.0-20.9 | 0 |
| 1-1422-A16/ 1-136-A1 | 2 | 25 | 19.5 | 0.77 | 18.4-22.3 | 2 |
| 1-1422-A5/ 2-340-A7 | | 68 | 21.2 | 1.75 | 17.3-27.2 | 4 |
| | 2 | 21 | 22.1 | 2.20 | 18.3-27.2 | 1 |
| | 3 | 24 | 19.8 | 0.91 | 17.3-21.0 | 3 |
| | 4 | 23 | 21.8 | 0.84 | 20.3-23.2 | 0 |
| 1-1422-A5/ 2-340-A8 | | 48 | 21.4 | 1.33 | 19.0-24.6 | 0 |
| | 1 | 21 | 21.3 | 0.77 | 20.1-22.6 | 0 |
| | 3 | 21 | 21.8 | 1.65 | 19.6-24.6 | 0 |
| | 4 | 6 | 20.4 | 1.29 | 19.0-22.4 | 0 |
| 1-1422-A5/ SCM3-7-3-A3 | | 121 | 19.5 | 1.51 | 17.2-26.0 | 23 |
| | 1 | 24 | 18.8 | 0.64 | 17.2-20.2 | 7 |
| | 2 | 24 | 18.7 | 0.68 | 17.2-20.1 | 10 |
| | 3 | 25 | 18.9 | 0.46 | 18.1-19.8 | 5 |
| | 4 | 23 | 21.8 | 1.88 | 19.0-26.0 | 0 |
| | 5 | 25 | 19.5 | 0.69 | 18.2-20.7 | 1 |
| 2-340-A5/ 1-136-A5 | | 57 | 20.5 | 0.74 | 19.0-22.2 | 0 |
| | 3 | 23 | 21.2 | 0.50 | 20.3-22.2 | 0 |
| | 4 | 34 | 20.1 | 0.54 | 19.0-21.1 | 0 |
| 2-340-A5/ 1-1422-A16 | | 91 | 20.7 | 0.97 | 17.9-23.0 | 2 |
| | 1 | 47 | 20.2 | 0.77 | 17.9-21.5 | 2 |
| | 4 | 20 | 21.8 | 0.78 | 20.1-23.0 | 0 |
| | 5 | 24 | 20.9 | 0.63 | 20.1-22.4 | 0 |
| 2-340-A5/ 1-1422-A5 | | 42 | 19.5 | 1.20 | 17.8-22.1 | 10 |
| | 1 | 17 | 20.7 | 0.67 | 19.7-22.1 | 0 |
| | 3 | 25 | 18.7 | 0.65 | 17.8-21.0 | 10 |

TABLE 14

Pearson correlation coefficient value of C16:0, C18:0, C18:1, and C18:2 of 547 F2 seeds.

| | Pearson Correlation Coefficient Value (r) N = 537 | | | |
|---|---|---|---|---|
| | C16:0 | C18:0 | C18:1 | C18:2 |
| C16:0 | 1.00 | | | |
| C18:0 | 0.01 ns | 1.00 | | |
| C18:1 | −0.30*** | −0.05 ns | 1.00 | |
| C18:2 | −0.16 | −0.24* | −0.84*** | 1.00 | y* = p < 0.05,
** = p < .01,
*** = p < .0001

Those skilled in the art will recognize that the methods and compositions of the present disclosure may be implemented in many manners and as such are not to be limited by the foregoing exemplary embodiments and examples. In this regard, any number of the features of the different embodiments, including cold tolerance and low palmitic acid content as described herein may be combined into single or multiple embodiments, and alternate embodiments having fewer than, or more than, all of the features described herein are possible.

Functionality may also be, in whole or in part, distributed among multiple components, in manners now known or to become known. Thus, myriad cultivars are possible in achieving the preferences described herein. Moreover, the scope of the present disclosure covers conventionally known manners for carrying out the described outcomes, as well as those variations and modifications that may be made as would be understood by those skilled in the art now and hereafter.

Furthermore, the embodiments of methods presented and described in the figures and tables in this disclosure are provided by way of example in order to provide a more complete understanding of the present disclosure. The disclosed methods are not limited to the operations and logical flow presented herein. Alternative embodiments are contemplated in which the presence or absence of one or more of the features occurs.

While various embodiments have been described for purposes of this disclosure, such embodiments should not be deemed to limit the teaching of this disclosure to those embodiments. Various changes and modifications may be made to the elements and processes described above to obtain a result that remains within the scope of the low palmitic lines described in this disclosure.

Representative seeds of the cotton lines of the present disclosure will be deposited under rule 37 C.F.R. 1.809, prior to issuance of a patent. Applicant will make a deposit of at least 2500 seeds of cotton lines disclosed herein with the American Type Culture Collection (ATCC), 10801 University Boulevard, Manassas, Va. 20110, USA, in accordance with the following: AFIS 1-136-A5, a seed sample of said cotton line having been deposited in ATCC Accession No. PTA-126033, under the Budapest Treaty, and access to such deposits will be available during the pendency of the application to the Commissioner of Patents and Trademarks and persons determined by the Commissioner to be entitled thereto upon request. All restrictions upon availability to the public will be irrevocably removed upon granting of the patent. The deposits will be maintained for a period of thirty years, or five years after the most recent request, or for the enforceable life of the patent, whichever is longer, and will be replaced if it becomes nonviable during that period. Applicant does not waive any rights granted under this patent or under the Plant Variety Protection Act (7 USC 2321 et seq.).

REFERENCES

Ashburner, M. 1990. Drosophilia: A Laboratory Manual. New York: Cold Spring Harbor Laboratory.

Auld, D. L., E. Bechere, M. Krifa, H. Kebede, E. Hequet, R, Wright, and S. Misra. 2007. Registration of 'Raider 276', a High-Yielding, Improved-Quality Upland Mutant Cotton Cultivar. J. Plant Reg. 1: 115-116.

Auld, D. L., G. G. Light, F. Mohaned, E. Bechere, and R. A. Allen. 2009. Mutagenesis Systems for Genetic Analysis of *Gossypium*. In Genetics and Genomics of Cotton (Plant Genetics and Genomics: Crops and Models), 1-18. New York: Springer.

Auld, D. L., M. D. Ethridge, J. K. Dever, and P. A. Dotray. 1998. Chemical Mutagenesis as a Tool in Cotton Improvement. Proc. Beltwide Cotton Conference. San Diego: National Cotton Council. 550-551.

Auld, D. L., M. K. Heikkinen, D. A. Erickson, J. L. Semyk, and J. E. Romero. 1992. Rapeseed Mutants with Reduced Levels of Polyunsaturated Fatty Acids and Increased Levels of Oleic Acid. Crop Sci. 32: 657-662.

Balyan, H. S., N. Sreenivasulu, O. Riera-Lizarazu, P. Azhaguvel, and S. F. Kianian. 2008. Mutagenesis and High-Throughput Functional Genomics in Cereal Crops: Current Status. Adv. Agron. 98: 357-414.

Bange, M. P. and S. P. Milroy. 2004. Impact of Short-Term Exposure to Cold Night Temperatures on Early Development of Cotton (*Gossypium hirsutum* L.). Australian J. Agr. Res. 55: 655.

Baud, S. and L. Lepiniec. 2010. Physiological and Developmental Regulation of Seed Oil Production. Prog. Lipid Res. 235-249.

Bilbro, J. D. and L. L. Ray. 1969. Differential Effect of Planting Date on Performance of Cotton Varieties on the High Plains of Texas. Texas Agr. Exp. Sta. MP-934.

Bilbro, J. D. and L. L. Ray. 1973. Effect of Planting Date on the Yield and Fiber Properties of Three Cotton Cultivars. Agron J. 606-609.

BizEE Degree Days—Weather Data for Energy Professionals. n.d. http://www.degreedays.net/(accessed Dec. 2, 2012).

Blackshear, J. and P. Johnson. 2003. Profitability of Irrigated Cotton-Grain Sorghum Rotations in the Southern High Plains of Texas. Beltwide Cotton Conferences. Nashville, Tenn. 474-480.

Bolek, Y. 2010. Predicting Cotton Seedling Emergence for Cold Tolerance: *Gossypium hirsutum* L. Not. Bot. Hort. Agrobot. 134-138.

Boman, R. and R. Lemon. 2005. Soil Temperatures for Cotton Planting. Texas Cooperative Extension-The Texas A&M University System.

Boquet, D. J. and E. L. Clawson. 2009. Cotton Planting Date: Yield, Seedling Survival, and Plant Growth. Agron J. 1123-1130.

Borth, T. D., D. R. Krieg, and G. M. Jividen. 1997. Genetic and Environmental Factors Affecting the Fatty Acid Composition of Polar and Non-Polar Lipids of Cottonseed. Proc. of the Beltwide Cotton Conference. 1455-1458.

Briggs, F. N. and P. F. Knowles. 1967. Introduction to Plant Breeding, Reinhold Publishing Corporation, (1967).

Brown, N. 20. Mutagenesis. Plant Breeding. Jun. 6, 2012. http://projects.coe.uga.edu/plantbreeding/index.php?title=20.Mutagenesis (accessed Jan. 26, 2013).

Buxton, D. R. and P. J. Sprenger. 1976. Genetic Variability for Cottonseed Germination at Favourable and Low Temperatures. Crop Sci. 16: 243-246.

Byrson, C. T., K. N. Reddy, and W. T. Molin. 2003. Purple Nutsedge (*Cyperus rotundus*) Population Dynamics in Narrow Row Transgenic Cotton (*Gossypium hirsutum*) and Soybean (*Glycine max*) Rotation. Weed Technol. 17: 807-810.

Camp, A. F. and M. N. Walker. 1927. Soil Temperature Studies with Cotton II. The Relation of Soil Temperature to Germination and Growth of Cotton. Florida Agricultural Experiment Station Bulletin.

Cantrell, R. G., C. L. Roberts, and C. Waddell. 2000. Registration of 'Acala 1517-99' Cotton. Crop Sci. 40: 1199-1200.

Chapman, K. D., S. Austin-Brown, S. A. Sparace, A. J. Kinney, K. G. Ripp, I. L. Pirtle, and R. M. Pirtle. 2001. Transgenic Cotton Plants with Increased Seed Oleic Acid Content. JAOCS 78:9, 941-947.

Christiansen, M. N. and R. Rowland. 1981. Cotton Physiology-Seed and Germination. Proc. of the Beltwide Cotton Conference. New Orleans, La.: NCCA. 315-318.

Christiansen, M. N. and R. O. Thomas. 1969. Season-Long Effects of Chilling Treatments Applied to Germinating Cottonseed. Crop Sci. 9: 672-673.

Christiansen, M. N. and R. P. Moore. 1959. Seed Coat Structural Differences that Influence Water Uptake and Seed Quality in Hard Seed Cotton. Agron. J. 51: 582-584.

Christiansen, M. N. 1968. Induction and Prevention of Chilling Injury to Radicle Tips of Imbibing Cottonseed. Plant Physiol. 43: 743-746.

Christidis, B. G. 1936. Cottonseed Treatment with Sulphuric Acid. J. Agric. Sci. 26: 648-663.

Clay, W. F., E. J. Bartowski, and F. R. H. Katterman. 1976. Nucleic Acid Metabolism and Fatty Acid Content During Chilling Stress in Germinating Cotton (*Gossypium barbadense* L.). Plant Physiol. 38: 171-175.

Colaizzi, P. D., S. R. Evett, and T. A. Howell. 2004. Irrigation Capacities and Methods for Cotton in the Northern High Plains. High Plains Groundwater Resources Conference. Lubbock, Tex.: TTU Water Resources Center. 154-162.

Cole, D. F. and J. E. Wheeler. 1974. Effect of Pregermination Treatments on Germination and Growth of Cottonseed at Suboptimal Temperatures. Crop Sci. 14: 451-454.

Database of Mutant Variety and Genetic Stocks. Food and Agriculture Organization/Int. Atomic Energy Agency (FAO/IAEA). n.d. http://mvgs.iaea.org/AboutMutant-Varities.aspx (accessed Jan. 26, 2013).

Dowd, M. K., D. L. Boykin, W. R. Meredith Jr., B. T. Campbell, F. M. Bourland, J. R. Gannaway, K. M. Glass, and J. Zhang. 2010. Fatty Acid Profiles of Cottonseed Genotypes from the National Cotton Variety Trials. J. Cotton Sci. 14: 64-73.

Esparza, A. M., P. H. Gowda, R. L. Baumhardt, T. H. Marek, and T. A. Howell. 2007. Heat Unit Availability for Cotton Production in the Ogallala Aquifer Region of the United States. J. Cotton Sci. 110-117.

Fehr, W. R. 2007. Breeding for Modified Fatty Acid Composition in Soybean. Crop Sci. (47(S3): S72-S87.

Funk, R. D., J. W. Mjelde, F. M. Hons, and V. A. Saladino. 1999. An Economic Analysis of a Corn-Soybean Crop Rotation Under Various Input Combinations in South Central Texas. J. Agr. Appl. Econ. 69-81.

Gazaway, W. S., J. R. Akridge, and K. Mclean. 2000. Impact of Various Crop Rotations and Various Winter Cover Crops on Reniform Nematode in Cotton. Proc. Beltwide Cotton Conferences. Memphis, Tenn.: NCCA. 162-163.

Gibson, J. R., LL. Ray, C. L. Flowers. 1969. Influence of Night Temperature on Seed Development of Five Varieties of Cotton. Proc. Beltwide Cotton Prod. Res. Conf. Proc. 117-118.

Green, A., S. Singh, and Q. Liu. Nov. 17, 2009. Modified Cottonseed Oil. U.S. Pat. No. 7,619,105.

Green, A. G. 1986. A Mutant Genotype of Flax (*Linum usitatissimum* L.) Containing Very Low Levels of Linolenic Acid in Its Seed Oil. Can. J. Plant Sci. 66: 499-503.

Greene, E. A., C. A. Codomo, N. E. Taylor, J. G. Henikoff, B. J. Till, S. H. Reynolds, L. C. Enns, C. Burtner, J. E. Johnson, A. R. Odden, L. Comai, and S. Henikoff. 2003. Spectrum of Chemically Induced Mutations from a Large-Scale Reverse-Genetic Screen in *Arabidopsis*. Genetics. 164: 731-740.

Hakoomat, A., M. N. Afzal, S. Ahmad, and D. Muhammad. 2009. Effect of Cultivars and Sowing Dates on Yield and Quality of *Gossypium hirsutum* L. Crop. J. Food Agric. Environ. 7: 244-247.

Hall, A. J. 2003. Evaluation of Fatty Acid Composition of Cotton Germplasm and Association with Cold Tolerance. Masters Thesis, Texas Tech University.

Johnson, W. C. III and B. G. Mullinix, Jr. 1997. Population Dynamics of Yellow Nutsedge (*Cyperus esculentus*) in Cropping Systems in the Southeastern Coastal Plain. Weed Sci. 45: 166-171.

Jones, A. H. M. Davies, and T. A. Voelker. 1995. Palmitoyl-Acyl Carrier Protein (ACP) Thioesterase and the Evolutionary Origin of Plant Acyl-ACP Thioesterases. Plant Cell. 7: 359-371.

Kargiotidou, A., T. Dell, D. Galanopoulou, A. Tsaftaris, and T. Farmaki. 2008. Low Temperature and Light Regulate Delta 12 Fatty Acid Desaturases (FAD2) at a Transcriptional Level in Cotton (*Gossypium hirsutum*). Journal of Experimental Botany. 59:8 2043-2056.

Kerby, T. A., S. Johnson, K. D. Hake, L. M. Carter, and R. H. Garber. 1996. Seed Quality and Planting Environment, eds Cotton Production Manual, Division of Agricultural and Natural Resources, University of California.

Kittock, D. L., B. B. Taylor, and W. C. Hofmann. 1987. Partitioning Yield Reduction from Early Cotton Planting. Crop Sci. 27: 1011-1015.

Krzyzanowski, F. C., and J. C. Delouche. 2011. Germination of Cotton Seed in Relation to Temperature. Rev. Bras. Sementes. 33: 543-548.

Larkin, P. J. 1998. Introduction. In Somaclonal Variation and Induced Mutations in Crop Improvement. 3-13. Kluwer Academic Publishers.

Linder, C. R. 2000. Adaptive Evolution of Seed Oils in Plants: Accounting for the Biogeographic Distribution of Saturated and Unsaturated Fatty Acids in Seed Oil. The American Naturalist. 156:442-458.

Liu, Q., S. Singh, K. Chapman, and A. Green. 2009. Bridging Traditional and Molecular Genetics in Modifying Cottonseed Oil. In Plant Genetics and Genomics: Crops and Models Vol 3. Genetics and Genomics of Cotton, by A. H. Paterson, 353-382.

Liu, Q., S. Surinder, K. Chapmena, and A. Green. 2009. Bridging Traditional and Molecular Genetics in Modifying Cottonseed oil. In. *Genetics and Genomics of Cotton*. A. H. Paterson (Ed.) Springer Science+Business Media, P. 353-382.

Liu, Q., S. P. Singh, and A. G. Green. 2002. High-Stearic and High-Oleic Cottonseed Oils Produced by Hairpin RNA-Mediated Post-Transcriptional Gene Silencing. Plant Physiol. 129: 1732-1743.

Locke, M. A., K. N. Reddy, and R. M. Zablotowica. 2002. Weed Management in Conservation Crop Production Systems. Weed Biol. Manage. 2: 123-132.

Lowery, C. C., D. L. Auld, E. Bechere, R. J. Wright, E. Hequet, N. Abidi, and C. W. Smith. 2007. Use of Chemical Mutagnesis in Improving Upland Cotton. World Cotton Research Conference.

Ludwig, C. A. 1932. The Germination of Cotton Seed at Low Temperature. J. Agr. Res. 44: 367-380.

Lyons, J. M. and C. M. Asmundson. 1965. Solidification of Unsaturated/Saturated Fatty Acid Mixtures and Its Relationship to Chilling Sensitivity in Plants. J. Am. Chem. Soc. 42: 1056-1058.

Marani, A. and A. Amirav. 1970. Effect of Delinting and of Genetical Factors on the Germination of Cotton Seeds at Low Temperatures. Crop Sci. 10: 509-511.

Marek, T. and D. Bordovsky. 2006. Performance of Ten Cotton Varieties in the Northern Texas High Plains. The Tex. J. Agr. Nat. Res. 19: 48-61.

McCallum, C. M., L. Comai, E. A. Greene, and S. Henikoff. 2000. Targeting Induced Local Lesions in Genomes (TILLING) for Plant Functional Genomics. Plant Physiol. 123: 439-442.

Meadows, S. A. 2012. Evolution of Seed Oil Melting Points of Multiple Species at a Commong Latitude. Masters Thesis. The University of Texas at Austin.

McDonald, B. A., J. Zhan, and J. J. Burdon. 1999. Genetic Structure of Phynchosporium secalis in Australia. APS. 89: 639-645.

Miquel, M. F. and J. A. Browse. 1994. High-Oleate Oilseeds Fail To Develop at Low Temperature. Plant Physiol. 106: 421-427.

Miquel, M. F., D. J. James, H. Donner, and J. Browse. 1993. *Arabidopsis* Requires Polyunsaturated Lipids for Low-Temperature Survival. Proc. Natl. Acad. Sci. USA. 6208-6212.

Misra, J. A. and S. K. Bondurant. 1999. An Analysis of the Cottonseed Pricing Structure in Texas. Proceedings of the Beltwide Cotton Conference. Memphis, Tenn.: National Cotton Council. 334-339.

Muller, H. 1928. The Production of Mutations by X-rays. Proc. of the National Academy of Sciences of the United States of America. 14: 714.

Murata, N. O., O. Ishizzaki-Nishizawa, S. Higashi, H. Hayashi, Y. Tasaka, and I. Nishida. 1992. Genetically Engineered Alteration in the Chilling Sensitivity of Plants. Nature. 356: 710-713.

National Agricultural Statistics Service. n.d. http://www-.nass.usda.gov/Data_and Statistics/Quick_Stats/(accessed Mar. 13, 2013).

NCPA: Cottonseed Oil. National Cottonseed Products Association. 2002. http://www.cottonseed.com/publications/csobro.asp (accessed Jan. 31, 2013).

New, L. and D. Dusek. 2004. Ogallala Aquifer 2004 Annual Report-Crop Irrigation and Production. Amarillo, Tex.: Texas. Coop. Ext. Serv.

Nishida, I. and Murata, N. O. 1996. Chilling Sensitivity in Plants and Cyanobackterial: The Crucial Contribution of Membrane Lipids. Annu. Rev. Plant Physiol. Plant Mo. Biol. 47:541-68.

Nonogaki, H., G. W. Bassel, and J. D. Bewley. 2010. Germination-Still a Mystery. Plant Sci. 574-581.

Oosterhuis, D. M., and J. Jernstedt. 1999. Morphology and Anatomy of the Cotton Plant. In Cotton: Origin, History, Technology and Production, by W. C. and J. T. Cothren Smith, 175-206. New York: John Wiley and Sons, Inc.

Pate, D. K., and J. W. Johnson. 2010. Economic Evaluation of Limited Irrigation Production Strategies on the Southern High Plains of Texas. Beltwide Cotton Conferences. New Orleans, La. 461-466.

Pelc, S. E. 2013. Determination of the Genetic Basis of Seed Oil Composition and Melting Point—Adaptive Quantitative Traits—and their Fitness Effects in *Arabidopsis thaliana*. Dissertation for Doctor of Philosophy. The University of Texas at Austin.

Peng, S., D. R. Krieg, and S. K. Hicks. 1989. Cotton Lint Yield Response to Accumulated Heat Units and Soil Water Supply. Field Crop Res. 461-466.

Pirtle, R. M., D. W. Yoder, T. T. Huynh, M. Nampaisansuk, I. L. Pirtle, and K. D. Chapman.. 1999. Characterization of a Palmitoyl-Acyl Carrier Protein Thioesterase (FatB1) in Cotton. Plant Cell Physiol. 155-163.

Primomo, V. S., D. E. Falk, G. R. Ablett, J. W. Tanner, and I Rajcan. 2002. Genotype X Environment Interactions, Stability, and Agronomic Performance of Soybean with Altered Fatty Acid Profiles. Crop Sci. 42:37-44.

Reddy, K. N. 2004. Weed Control and Species Shifts in Bromoxynil and Glyphosate Resistant Cotton (Gassypium *hirsutum*) Rotation Systems. Weed Technol. 18: 131-139.

Reddy, K. N., M. A. Locke, C. H. Koger, R. M. Zablotowica. 2006. Cotton and Corn Rotation Under Reduced Tillage Management: Impacts on Soil Properties, Weed Control, Yield, and Net Return. Weed Sci. 768-774.

Ryavalad, S., N. K. Biradarpatil, R. S. Giraddi, and I. S. Katageri. 2009. Effect of Acid Delinting Seed Treatment and Containers on Storability of Cotton Hybrid. Karnataka J. Agric. Sci. 22: 56-60.

Sansone, C., T. Isakeit, R. Lemon, and B. Warrick. 2002. Texas Cotton Production: Emphasizing Integrated Pest Management. Texas Coop. Ext. Serv, College Station, Tex.: TAMU.

Sawan, Z. M., S. A. Hafez, and A. E. Basyony. 2001. Effect of Nitrogen Fertilization and Foliar Application of Plant Growth Retardants and Zinc on Cottonseed, Protein and Oil Yields and Oil Properties of Cotton. J. Agron. Crop Sci. 186: 183-191.

Segarra, E., J. W. Keeling, and J. R. Abernathy. 1991. Tillage and Croppig System Effects on Cotton Yield and Profitability on the Texas Southern High Plains. J. Prod. Agric. 4: 566-571.

Simpson, D. M., C. L. Adams, and G. M. Stone. 1940. Anatomical Structure of the Cottonseed Coat as Related to Problems of Germination. Technical Bulletin No. 734, Washington, D.C.: USDA.

Smith, C. 2003. Registration of TAM 94-L-25 and TAM 94J-3 Germplasm Lines of Upland Cotton with Improved Fiber Length. Crop Sci. 43: 742-743.

Speed, T. R. 1995. Genetic and Environmental Influences on Cold Tolerance of Cotton Seedling Germination. Masters Thesis, Lubbock, Tex.: Texas Tech University.

Stoller. E. W. and E. J. Weber. 1975. Differential Cold Tolerance, Starch, Sugar, Protein, and Lipid of Yellow and Purple Nutsedge Tubers. Plant Physiol. 55: 859-863.

Styles, B. 2003. Effects of Seed Processing Methods on Germination and Early Seedling Development of Cotton. Masters Thesis, University of Tennessee at Martin.

Texas Agrilife Extension Service. 2012 Texas Crop and Livestock Budgets: District I. n.d. http://agecoexttamu.edu/resources/crop-livestock-budgets/by-district/district-1/2012.html (accessed Dec. 12, 2012).

Texas Tech University West Texas Mesonet. n.d. http://www.mesonet.ttu.edu/(accessed Mar. 10, 2013).

Thomas, S. R., J. Sanchez, and J. B. Mudd. 1987. Factors Affecting the Fatty Acid Composition of Phosphatidylglycerol as Related to Chilling Sensitivity in Higher Plants. Metabolism Structure, and Function of Plant Lipids. 283-291.

Tuck, C. A., D. K. Y. Tan, M. P. Bange, W. N. Stiller. 2010. Cold-Tolerance Screening for Cotton Cultivars Using Germination Chill Protocols. Australian Agronomy Conference. Aust. Soc. Agron.

Vaidya, K. R. and M. M. Young. 1993. Ethyl Methanesulfonate Induced Variation in Qualitative and Quantitative Characters of Roselle (*Hibiscus sabdariffa* L.) (Malvaceae). Brazil. J. Genetics. 381-391.

Wang, C. Y. 1990. Chilling Injury of Horticultural Crops. CRC Press, Inc. Boca Raton, Fla.

Wanjura, D. F., E. B. Hudspeth, and J. D. Bilbro. 1969. Emergence Time, Seed Quality, and Planting Depth Effects on Yield and Survival of Cotton (*Gossypium hirsutum* L.). Agron. J. 61: 63-65.

Wanjura, F. D., D. R. Upchurch, J. R. Mahan, and J. J. Burke. 2002. Cotton Yield and Applied Water Relationships Under Drip Irrigation. Agricultural Water Management. 55:217-237.

Wendel, J. F. 1989. New World Tetraploid Cottons Contain Old-World Cytoplasm. Proc Natl Acad Sci. USA. 86: 4132-4136.

Wesley, R. A., C. D. Elmore, and S. R. Spurlock. 2001. Deep Tillage and Crop Rotation Effects on Cotton, Soybean, and Grain Sorghum on Clayey Soils. Agron. J. 93: 170-178.

Wesley, R. A., L. G. Heatherly, C. D. Elmore, and S. R. Spurlock. 1994. Effects of Crop Rotation and Irrigation on Soybean and Wheat Doublecropping on Clay Soil, an Economic Analysis. Springfield, Va.: USDA, Agricultural Research Service.

Windham, G. L. and G. W. Lawrence. 1992. Host Status of Commercial Maize Hybrids to *Rotylenchulus reniformis*. J. of Nematol. 24: 745-748.

Wrather, J. A., B. J. Phipps, W. E. Stevens, and A. S. Phillips. 2005. Cotton Planting Date and Plant Population Effects on Yield and Quality in the Mississippi Delta. Portageville, Mo.

What is claimed is:

1. A cotton seed of a cotton line, wherein the cotton line is AFIS 1-136-A5, a seed sample of said cotton line having been deposited in ATCC Accession No. PTA-126033, and wherein the cotton seed comprises low palmitic acid content.

2. A cotton plant of a cotton line AFIS 1-136-A5, a cotton seed sample of said cotton line having been deposited in ATCC Accession No. PTA-126033.

3. A plant part of the plant of claim 2.

4. A tissue culture of protoplasts or cells from the plant of claim 2, wherein said protoplasts or cells are produced from a plant part selected from the group consisting of leaf, pollen, ovule, embryo, cotyledon, hypocotyl, meristematic cell, fiber, root, root tip, pistil, anther, flower, seed, shoot, stem, pod and petiole.

5. A method of producing a cotton plant having an added desired trait, wherein the method comprises introducing a transgene conferring the desired trait into the cotton plant of claim 2.

6. The method of claim 5, wherein the desired trait is at least one of male sterility, herbicide tolerance, insect or pest resistance, disease resistance, modified fatty acid metabolism, modified carbohydrate metabolism or modified cotton fiber characteristics.

7. The method of claim 6, wherein the desired trait is herbicide tolerance and the tolerance is conferred to an herbicide which is glyphosate, sulfonylurea, imidazolinone, dicamba, glufosinate, phenoxy proprionic acid, cyclohexanedione, triazine, benzonitrile, bromoxynil, or combinations thereof.

8. The method of claim 6, wherein the desired trait is insect resistance and the transgene encodes a *Bacillus thuringiensis* (Bt) endotoxin.

9. A method for producing a cotton seed, said method comprising crossing two cotton plants and harvesting the resultant cotton seed, wherein at least one of said cotton plants is a cotton line AFIS 1-136-A5, a seed sample of said cotton line having been deposited in ATCC Accession No. PTA-126033.

10. A cotton seed produced by the method of claim 9.

11. A cotton plant, or a part thereof, produced by growing said cotton seed of claim 10.

12. The cotton seed of claim 10, wherein the cotton seed contains low palmitic acid content.

13. The method of claim 9, wherein the cotton line AFIS 1-136-A5 contains cotton seeds with low palmitic acid content.

14. The method of claim 13, wherein the cotton line AFIS 1-136-A5 produces cotton seed comprising the low palmitic acid content of less than 20% of the total oil content of the cotton seed.

15. The method of claim 13, wherein the cotton line AFIS 1-136-A5 produces cotton seed comprising the palmitic acid content of between 17.8% and 19.8% of the total oil content of the cotton seed.

16. A method of introducing a desired trait into commercial cotton cultivar, the method comprising:
    (a) crossing a commercial cotton cultivar with low palmitic acid cotton line AFIS 1-136-A5, a seed sample of said cotton line having been deposited in ATCC Accession No. PTA-126033;
    (b) selecting one or more progeny plants that have the desired trait;
    (c) backcrossing the selected progeny plants with the selected low palmitic acid mutant line in (a) above;
    (d) selecting for backcross progeny plants that have the desired trait; and
    (e) repeating steps (c) and (d) two or more times in succession to produce selected third or higher backcross progeny plants that comprise the desired trait of the low palmitic acid cotton line selected in (a) above.

17. The method of claim 16, wherein the cotton cultivar produces cotton seeds with low palmitic acid content.

18. The method of claim 16, wherein the cotton cultivar produces seed having the low palmitic acid content of less than 20% of the total oil content of the cotton seed.

19. The method of claim 16, wherein the cotton cultivar produces seed having the low palmitic acid content of between 17.8% and 19.8% of the total oil content of the cotton seed.

* * * * *